US006844431B1

(12) United States Patent
Pulst

(10) Patent No.: US 6,844,431 B1
(45) Date of Patent: Jan. 18, 2005

(54) NUCLEIC ACID ENCODING SPINOCEREBELLAR ATAXIA-2 AND PRODUCTS RELATED THERETO

(75) Inventor: Stefan M. Pulst, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 523 days.

(21) Appl. No.: 08/981,998

(22) PCT Filed: May 8, 1997

(86) PCT No.: PCT/US97/07725

§ 371 (c)(1),
(2), (4) Date: May 11, 1998

(87) PCT Pub. No.: WO97/42314

PCT Pub. Date: Nov. 13, 1997

Related U.S. Application Data

(63) Continuation-in-part of application No. 08/727,084, filed on Oct. 8, 1996, now abandoned.
(60) Provisional application No. 60/022,207, filed on Jul. 19, 1996, and provisional application No. 60/017,388, filed on May 8, 1996.

(51) Int. Cl.[7] ........................... C07H 21/04; C12Q 1/68
(52) U.S. Cl. ................ 536/23.1; 536/24.31; 536/24.33; 435/6; 435/320.1
(58) Field of Search ...................... 435/6, 172.3, 320.1, 435/325; 536/23.5, 24.31, 24.33

(56) References Cited

U.S. PATENT DOCUMENTS

| | | | | |
|---|---|---|---|---|
| 5,155,218 A | * | 10/1992 | Weinshank et al. | ............ 536/27 |
| 5,552,282 A | | 9/1996 | Caskey et al. | .................. 435/6 |
| 5,650,270 A | | 7/1997 | Giese et al. | .................... 435/6 |
| 5,650,277 A | | 7/1997 | Navot et al. | .................... 435/6 |
| 5,741,645 A | | 4/1998 | Orr et al. | ........................ 435/6 |
| 5,853,995 A | * | 12/1998 | Lee | ................................ 435/6 |
| 5,885,834 A | * | 3/1999 | Epstein | ....................... 435/375 |
| 6,251,589 B1 | | 6/2001 | Tsuji et al. | |

FOREIGN PATENT DOCUMENTS

| | | | | |
|---|---|---|---|---|
| WO | WO 95/01437 | | 1/1995 | |
| WO | WO 97/17445 | | 5/1997 | |
| WO | WO 97/18224 | * | 5/1997 | ........... C07H/17/00 |

OTHER PUBLICATIONS

Sahba et al. "Genomic Structure of the human gene for spinocerebellar ataxia type 2 (SCA2) on chromosome 12q24.1" Genomics, vol. 47, pp. 359–364, 1998.*
Chouhry et al. "CAG repeat instability at SCA2 locus: anchoring CAA interruptions and linked single nucleotide polymorphisms" Human Molecular Genetics. vol. 1, No. 21, pp. 2437–3446, Oct. 2001.*

Mizushima et al. "Analysis of spinocerebellar ataxia type 2 gnee and haplotype analysis (CCG)1–2 polymorphism and contribution to founder effect". J. of Medical Genetics. vol. 36, No. 2, pp. 112–114, Feb. 1999.*
Sanpei et al. "Direct detection of expanded (CAG/CTG) repeats." Biochemical and Biophysical Research Communications. vol. 212, No. 2 p. 341–346, Jul. 1995.*
IntelliGenetics Comparison of SEQ ID NO: 2 &4 and SEQ ID NO: 3& 5.*
GenBank Accession No. Y08262, Imbert et al. Sep. 1996.*
GenBank Accession No. T78912, Lutz et al. May 1997.*
GenBank Accession No. A62706, Tora et al. May 1997.*
GenBank Accession No. AA476524, Hillier et al. Jan. 1995.*
GenBank Accession No. L27350, Ambrose et al. 1994.*
GenBank Accession No. U70323, Pulst et al. 1996.*
GenBank Accession No. AF041472, Nechiporuk et al. Jan. 1998.*
Perkin–Elmer Biotechnology Catolog, 1992–1993, p. 11–12.*
Filla et al. "Has Spinocerebellar ataxia type 2 a distinct phenotype?" Neurology, Apr. 1995, p. 793–796.*
Banfi, et al., "Identification and characterization of the gene causing type 1 spinocerebellar ataxia," *Nature Genetics*, 7, 513–519 (1994).
Belal et al., "Clinical and genetic analysis of a Tunisian family with autosomal dominant cerebellar ataxia type 1 linked to the SCA2 locus," *Neurology*, 44, 1423–1426 (1994).
Brook, "Retreat of the triplet repeat," *Nat. Genet.*, 3, 279–281 (1993).
Brunner et al., "Brief Report: Reverse Mutation In Myotonic Dystrophy," *New Engl. J. Med.*, 328, 476–480 (1993).
Filla et al., "Prevalence of hereditary ataxias and spastic paraplegias in Molise, a region of Italy," *J. Neurol.*, 239, 351–353 (1992).
Gispert et al., "Chromosomal assignment of the second locus for autosomal dominant cerebellar ataxia (SCA2) to chromosome 12q23–24.1," *Nat. Genet.*, 4, 294–299 (1993).

(List continued on next page.)

Primary Examiner—Jeanine Goldberg
(74) Attorney, Agent, or Firm—Jones Day

(57) ABSTRACT

The present invention provides isolated nucleic acids encoding human SCA2 protein, or fragments thereof, and isolated SCA2 proteins encoded thereby. Further provided are vectors containing invention nucleic acids, probes that hybridize thereto, host cells transformed therewith, antisense oligonucleotides thereto and compositions containing antibodies that specifically bind to invention polypeptides, as well as transgenic non-human mammals that express the invention protein. In addition, methods for diagnosing spinocerebellar Ataxia Type 2 are provided.

8 Claims, 14 Drawing Sheets

OTHER PUBLICATIONS

Imbert, "Cloning of the gene for spinocerebellar ataxia 2 reveals a locus with high sensitivity to expand CAG/glutamine repeats," *Nature Genetics, 14,* 285–291(1996).

Ioannou et al., "A new bacteriophage P1–derived vector for the propagation of large human DNA fragments," *Nat. Genet., 6,* 84–89 (1994).

Kawaguchi et al., "CAG expansions in a novel gene for Machado–Joseph disease at chromosome 14q32.1," *Nat. Genet., 8,* 221–227 (1994).

Koide et al., "Unstable expansion of CAG repeat in hereditary dentatorubral–pallidoluysian atrophy (DRPLA)," *Nat. Genet., 6,* 9–13 (1994).

Kremer, et al., "Mapping of DNA Instability at the Fragile X to a Trinucleotide Repeat Sequence p(CCG)n," *Science, 252,* 1711–1714 (1991).

Lopes–Cendes et al., "Confirmation of the SCA–2 Locus as an Alternative Locus for Dominantly Inherited Spinocerebellar Ataxias and Refinement of the Candidate Region," *Am. J. Hum. Genet., 54,* 774–781 (1994).

MacDonald et al., "A Novel Gene Containing a Trinucleotide Repeat That Is Expanded and Unstable on Huntington's Disease Chromosomes," *Cell, 72,* 971–983 (1993).

Mahadevan, et al., "Myotonic Dystrohpy Mutation: An Unstable CTG Repeat in the 3' Untranslated Region of the Gene," *Science, 255,* 1253–1255 (1992).

Mandel, "Questions of expansion," *Nat. Genet., 4,* 8–9 (1993).

Nagafuchi et al., "Dentatorubral and pallidoluysian atrophy expansion of an unstable CAG trinucleotide on chromosome 12p,"*Nat. Genet., 6,* 14–18 (1994).

Orr et al., "Expansion of an unstable trinucleotide CAG repeat in spinocerebellar ataxia type 1," *Nat. Genet., 4,* 221–226 (1993).

Polo et al., "Heredetiary Ataxias and Paraplegias in Cantabria, Spain," *Brain, 114,* 855–866 (1991).

Pulst et al., "Anticipation in spinocerebellar ataxia type 2," *Nat. Genet., 5,* 8–10 (1993).

Pulst et al., "Genetic and Physical Map of the Spinocerebellar Ataxia 2 (SCA2) Region on Human Chromosome 12," *Neurology, 45,* A422 (1995).

Pulst et al., "Moderate expansion of a normally biallelic trinucleotide repeat in spinocerebellar ataxia type 2," *Nature Genetics, 14,* 269–276 (1996).

Ranum et al., "Spinocerebellar ataxia type 5 in a family descended from the grandparents of President Lincoln maps to chromosome 11," *Nat. Genet., 8,* 280–284 (1994).

Rubensztein, et al., Phenotypic Characterization of Individuals with 30–40 CAG Repeats in the Huntington Disease (HD) Gene Reveals HD Cases with 36 Repeats and Apparently Normal Elderly Individuals with 36–39 Repeats, *Am. J. Hum. Genet., 59,* 16–22 (1996).

Sanpei et al., "Identification of the spinocerebellar ataxia type 2 gene using a direct identification of repeat expansion and cloning technique, DIRECT," *Nature Genetics, 14,* 277–284 (1996).

Stevanin et al., "Screening for proteins with polyglutamine expansions in autosomal dominant cerebellar ataxias," *Human Molecular Genetics, 5,* 1887–1892 (1996).

Takiyama et al., "The gene for Machado–Joseph disease maps to human chromosome 14q," *Nat. Genet., 4,* 300–304 (1993).

The WashU–Merck EST Project, "Soares parathyroid tumor NbHPA *Homo sapiens* cDNA clone," Accession No. W39162, May 15, 1996.

Trottier et al., "Polyglutamine expansions as a pathological epitope in Huntington's disease and four dominant cerebellar ataxias," *Letters to Nature, 378,* 403–406 (1995).

\* cited by examiner

```
  1  TTGGTAGCAACGGAAACGGCGGCGGCGCGTTTCGGCCCGGCTCCCGGCGGCTCCTTGGTC

61  TCGGCGGGCCTCCCCGCCCCTTCGTCGTCGTCCTTCTCCCCCTCGCCAGCCCGGGCGCCC

121  CTCCGGCCGCGCCAACCCGCGCCTCCCCGCTCGGCGCCCGTGCGTCCCCGCCGCGTTCCG

181  GCGTCTCCTTGGCGCGCCCGGCTCCCGGCTGTCCCCGCCCGGCGTGCGAGCCGGTGTATG
           SCA2-A
241  GGCCCCTCACCATGTCGCTGAAGCCCCAGCAGCAGCAGCAGCAGCAGCAACAGCAGC
                                                        SCA2-B
301  AGCAGCAACAGCAGCAGCAGCAGCAGCAGCAGCCGCCGCCCGCGGCTGCCAATGTCCGCA

361  AGCCCGGCGGCAGCGGCCTTCTAGCGTCGCCCGCCGCCGCGCCTTCGCCGTCCTCGTCCT

421  CGGTCTCCTCGTCCTCGGCCACGGCTCCCTCCTCGGTGGTCGCGGCGACCTCCGGCGGCG
                                  ↓
481  GGAGGCCCGGCCTGGGCAG GTGGGTGTCGGCACCCC
```

FIG. 2

```
  1  ACCCCCGAGAAAGCAACCCAGCGCGCCGCCGCTCCTCAGTGTCCCTCCGGCCCGGG           60
 61  GCCACCCTCAGCGTTCTGCTTCCGTCTTCCGTCTGACCCCTTCCGGTAAAGAGTCCCTATCCG 120
                          *
121  CACCTCCGCTCCCACCCGGCGCGCCCTCGGCGCCGCCCCTCCGATGCGCTCAGCGGCCGCA   180
                                              M  R  S  A  A  A        6
181  GCTCCTCGGAGTCCCGCGGTGGCCACCGAGTCTCGCCGTTCGCCCAGCCAGGTGGCCC      240
  7   A  P  R  S  P  A  V  A  T  E  S  R  R  F  A  A  A  R  W  P     26
241  GGGTGGCGCTCGTCCAGCGGCCGGGCGGGGAGCGGCGGGCGGTGGCGCGGGCC            300
 27   G  W  R  S  L  Q  R  P  A  R  R  S  G  R  G  G  G  A  A        46
301  CCGGGACCCGTATCCCTCCCCGCCCCCCCGGCCCCCCCCGGGCCCCCCTCCCGG           360
 47   P  G  P  Y  P  S  A  A  P  P  P  G  P  P  P  P  S  R           66
361  CAGAGCTCGCCTCCCTCCGCTCAGACTGTTTTGGTAGCAACGGCAACGGGGGGGCG         420
 67   Q  S  S  P  P  S  A  S  D  C  F  G  S  N  G  N  G  G  A        86
421  TTTCGGCCCGGCTCCCGGCTCCTGGTCTCGGGGGCCTCCCCGCCCCTTCGTC             480
 87   F  R  P  G  S  R  R  L  L  G  L  G  P  P  R  P  F  V  V       106
481  GTCCTTCTCCCCTGCCAGCCCCGCCGCCAACCCGGCCTCCCG                       540
107   V  L  L  P  L  A  S  P  G  A  P  P  A  A  P  T  R  A  S  P    126
541  CTCGGGGCGCCCGTCCCCCGCCGTTCCGGCGTCTCCTTGGCCCGGCTCCCGGC            600
127   L  G  A  R  A  S  P  P  R  S  G  V  S  L  A  R  P  A  P  G    146
                                          SCA2-A
601  TGTCCCCGCCCGGCGTGCGAGCCGGTGTATGGGCCCCTCACCATGTCGCTGAAGCCCCAG    660
147   C  P  R  P  A  C  E  P  V  Y  G  P  L  T  M  S  L  K  P  Q    166
661  CAGCAGCAGCAGCAGCAGCAGCAACAGCAGCAGCAGCAGCAGCAGCAG                720
167   Q  Q  Q  Q  Q  Q  Q  Q  Q  Q  Q  Q  Q  Q  Q  Q                186
```

FIG. 6A

```
                           SCA2-B
721   CAGCCGCCGCCGGGCTGCCAATGTCCGCAAGCCCGGCGGCCAGCGGCCTTCTAGCGTCG    780
187    Q  P  P  P  A  A  A  N  V  R  K  P  G  G  S  G  L  L  A  S   206
781   CCCGGCCGCCCGGCCCTTCGCCGTCCTCGTCCTCGTCCTCGGCCTCGGCCACGGCTCCC    840
207    P  A  A  P  S  P  S  S  S  S  V  S  S  S  S  A  T  A  P     226
841   TCCTCGGTGGTCGCGGCGACCTCCGGCGGAGCCCGGCCCGGCCAGAGGTCGAAAC        900
227    S  S  V  V  A  A  T  S  G  G  R  P  G  L  G  R  G  R  N      246
901   AGTAACAAAGGACTGCCTCAGTCTACGATTTCTTTTGATGGAATCTATGCAAATATGAGG   960
247    S  N  K  G  L  P  Q  S  T  I  S  F  D  G  I  Y  A  N  M  R   266
961   ATGGTTCATATACTTACACATCAGTTGTTGGCTCCAAATGTGAAGTACAAGTGAAAAATGGA 1020
267    M  V  H  I  L  T  S  V  V  G  S  K  C  E  V  Q  V  K  N  G   286
                                                    SCA2-14B
1021  GGTATATATGAAGGAGTTTTTAAAACTTACAGTCCGAAGTGTGATTTGGTACTTGATGCC  1080
287    G  I  Y  E  G  V  F  K  T  Y  S  P  K  C  D  L  V  L  D  A   306
1081  GCACACATGAGAAAAGTACAGAATCCAGTTCGGGGCCGAAACGTGAAGAAATAATGGAGAGT 1140
307    A  H  E  K  S  T  E  S  S  S  G  P  K  R  E  E  I  M  E  S   326
1141  ATTTTGTTCAAATGTTCAGACTTTGTTGTGGTACAGTTTAAAGATATGGACTCCAGTTAT  1200
327    I  L  F  K  C  S  D  F  V  V  V  Q  F  K  D  M  D  S  S  Y   346
1201  GCAAAAGAGATGCTTTTACTGACTGATAGCGCTATCAGTGCTAAAGTGAATGGCGAACACAAA 1260
347    A  K  R  D  A  F  T  D  S  A  I  S  A  K  V  N  G  E  H  K   366
1261  GAGAAGGACCTGGAGCCCTGGGATGCAGGTGAACTCACAGCCAATGAGGAACTTGAGGCT  1320
367    E  K  D  L  E  P  W  D  A  G  E  L  T  A  N  E  E  L  E  A   386
1321  TTGGAAAATGACGTATCTAATGGATGGGATCCCAATGATATTGTTCGATATAATGAAGAA  1380
387    L  E  N  D  V  S  N  G  W  D  P  N  D  M  F  R  Y  N  E  E   406
1381  AATTATGGTAGTGTCTACGTATGATAGCAGTTTATCTTCGTATACAGTGCCCTTAGAA    1440
407    N  Y  G  V  S  T  Y  D  S  S  L  S  S  Y  T  V  P  L  E     426
1441  AGAGATAACTCAGAAGAATTTTTAAAACGGGAAGCAAGGGCAAACCAGTTAGCAGAAGAA  1500
427    R  D  N  S  E  E  F  L  K  R  E  A  R  A  N  Q  L  A  E  E   446
```

FIG. 6B

```
1501 ATTGAGTCAAGTGCCCAGTACAAAGCTCGAGTGCCCTGAAAATGATGATAGGAGTGAG 1560
 447  I  E  S  S  A  Q  Y  K  A  R  V  A  L  E  N  D  D  R  S  E   466
1561 GAAGAAAAATACACAGCAGTTCAGAGAAATTCCAGTGAACGTGAGGGCACAGCATAAAC 1620
 467  E  E  K  Y  T  A  V  Q  R  N  S  S  E  R  E  G  H  S  I  N   486
1621 ACTAGGGAAAATAATAATATATTCCCTGACACAAGAAATAGAGAAGTCATATCCTGGGGA 1680
 487  T  R  E  N  K  Y  I  P  P  G  Q  R  N  R  E  V  I  S  W  G   506
1681 AGTGGGAGACAGAATTCACCGCGTATGGGCCAGCCTGGATCGGGCTCCATGCCATCAAGA 1740
 507  S  G  R  Q  N  S  P  R  M  G  Q  P  G  S  G  S  M  P  S  R   526
1741 TCCACTTCTCACACTTCAGATTTCAACCCGAATTCTGTTCAGACCAAAGAGTAGTTAAT 1800
 527  S  T  S  H  T  S  D  F  N  P  N  S  G  S  D  Q  R  V  V  N   546
1801 GGAGGTGTTCCCTGGCCATCGCCTTGCCCATCTCCTCCTGCCCACTTCTCTGCTAC 1860
 547  G  G  V  P  W  P  S  P  C  P  S  S  R  P  P  S  R  Y   566
1861 CAGTCAGGTCCCAACTCTCTTCCACCTCGGGCAGCCACCCTACACGGCGCCCTCCAGG 1920
 567  Q  S  G  P  N  S  L  P  P  R  A  A  T  P  T  R  P  P  S  R   586
1921 CCCCCCTCGCGGCCATCCAGACCCCCGTCTCACCCCTGCTCATGGTTCTCCAGCTCCT 1980
 587  P  P  S  R  P  S  R  P  P  S  H  P  S  A  H  G  S  P  A  P   606
1981 GTCTCTACTATGCCTAAACGCATGTCTTCAGAAGGCCTCCAAGGATGTCCCAAAGGCC 2040
 607  V  S  T  M  P  K  R  M  S  S  E  G  P  P  R  M  S  P  K  A   626
2041 CAGCGACATCCTCGAAATCACAGAGTTTCTGCTGGAGGGTTCCATATCCAGTGGCCTA 2100
 627  Q  R  H  P  R  N  H  R  V  S  A  G  R  G  S  I  S  S  G  L   646
2101 GAATTTGTATCCCACAACCCACCAAGTGAAGCAGCAGCTACTCCTCCAGTAGCAAGGACCAGT 2160
 647  E  F  V  S  H  N  P  P  S  E  A  A  T  P  P  V  A  R  T  S   666
2161 CCCTCGGGGGAACGTGTCATCAGTGGTCAGTGGTCGAGATTATCCCTAAAACT 2220
 667  P  S  G  G  T  W  S  S  V  V  S  G  V  P  R  L  S  P  K  T   686
2221 CATAGACCCAGGTCTCCCAGAACAGTATTGAAATACCCCAGTGGCCAGTTCTT 2280
 687  H  R  P  R  S  P  R  Q  N  S  I  G  N  T  P  S  G  P  V  L   706
```

FIG. 6C

```
2281  GCTTCTCCCCAAGCTGTGTATTATTCCAACTGAAGCTGTTGCCATGCCTATTCCAGCTGCA  2340
 707   A   S   P   Q   A   G   I   I   P   T   E   A   V   A   M   P   I   P   A   A    726
2341  TCTCCTACGCCTGCTAGTCCTGCATCGAACAGAGCTGTTACCCCTTCTAGTGAGGCTAAA  2400
 727   S   P   T   P   A   S   P   A   S   N   R   A   V   T   P   S   S   E   A   K    746
2401  GATTCCAGGCTTCAAGATCAGAGCAGAACTCCTCTGCAGGAATAAAGAAAATATTAAA  2460
 747   D   S   R   L   Q   D   Q   R   Q   N   S   P   A   G   N   K   E   N   I   K    766
2461  CCCAATGAAACATCACCTAGTTCTCAAAAGCTGAAAACAAGTATATCACCAGTGTT    2520
 767   P   N   E   T   S   P   S   F   S   K   A   E   N   K   G   I   S   P   V   V    786
2521  TCTGAACATAGAAAACAGATTGATGATTTAAGAATGATTTAGGTTACAG          2580
 787   S   E   H   R   K   Q   I   D   D   L   K   K   F   K   N   D   F   R   L   Q    806
2581  CCAAGTTCTACTTCTGAATCTATGGATCAAAATGAACAAGTGCTAAGGATTCTTTCATTGAAAT  2640
 807   P   S   S   T   S   E   S   M   D   Q   L   L   N   K   N   R   E   G   E   K    826
2641  TCAAGAGATTTGATCAAAGACAAAATTGAACCAAGTGCTAAGGATTCTTTCATTGAAAAT  2700
 827   S   R   D   L   I   K   D   K   I   E   P   S   A   K   D   S   F   I   E   N    846
2701  AGCAGCAGCAACTGTACCAGTGGCAGCAGCAGCCGAATAGCCCCAGCATTTCCCCTTCA  2760
 847   S   S   S   N   C   T   S   G   S   S   K   P   N   S   P   S   I   S   P   S    866
2761  ATACTTAGTAACACGGAGCACAAGAGAGGGACCTGAGGTCACTTCCCAAGGGGTTCAGACT  2820
 867   I   L   S   N   T   E   H   K   R   G   P   E   V   T   S   Q   G   V   Q   T    886
2821  TCCAGCCCAGCATGTAAACAGGAGAAAGACGATAAGGAAGAGAAGAAAGACGCAGCTGAG  2880
 887   S   P   A   C   K   Q   E   K   D   D   K   E   E   K   K   D   A   A   E    906
2881  CAAGTTAGGAAATCAACATTGAATCCAAATGCAAAGGAGTTCAACCTAGCCCATCT    2940
 907   Q   V   R   K   S   T   L   N   P   N   A   K   E   F   N   P   R   S   F   S    926
2941  CAGCCAAAGCCTTCTACTACCCCAACTTCACCTGGCCTCAAGCACACAACTAGCCCATCT  3000
 927   Q   P   K   P   S   T   T   P   T   S   P   R   P   Q   A   Q   P   S   P   S    946
3001  ATGGTGGGTCATCAACAGCCAACTCCAGTTTATACTCCAGTTTGTTTTGCACCAAAT   3060
 947   M   V   G   H   Q   Q   P   T   P   V   Y   T   Q   P   V   C   F   A   P   N    966
3061  ATGATGTATCCAGTCCCAGTGAGCCCTGCAACCTTTATACCCAATACCTATGACG      3120
 967   M   M   Y   P   P   V   S   P   G   V   Q   P   L   Y   P   P   I   P   M   T    986
```

FIG. 6D

```
3121  CCCATGCCAGTGAATCAAGCCAAGACATATAGAGCAGTACCAAATATGCCCCAACAGCGG  3180
 987  P  M  P  V  N  Q  A  K  T  Y  R  A  V  P  N  M  P  Q  Q  R   1006
3181  CAAGACCAGCATCATCAGAGTGCCATGATGCACCCAGCGTCAGCGGGCCAGGCCCACCGATT 3240
1007  Q  D  Q  H  H  Q  S  A  M  M  H  P  A  S  A  A  G  P  P  I   1026
3241  GCAGCCACCCCAGCTTACTCCACGCAATATGTGCCTACAGTCCTCAGCAGTTCCCA      3300
1027  A  A  T  P  P  A  Y  S  T  Q  Y  V  A  Y  S  P  Q  Q  F  P   1046
3301  AATCAGCCCCTTGTTCAGCATGTGCCACATTATCAGTCTCAGCATCCTCATGTCTATAGT  3360
1047  N  Q  P  L  V  Q  H  V  P  H  Y  Q  S  Q  H  P  H  V  Y  S   1066
3361  CCTGTAATACAGGGTAATGCTAGAATGATGGCACCACCAACACGCCCAGCCTGGTTTA    3420
1067  P  V  I  Q  G  N  A  R  M  M  A  P  P  T  H  A  Q  P  G  L   1086
3421  GTATCTTCTTCAGCAACTCAGTACGGGCTCATGAGCAGCATGCGATGTATGCATGT      3480
1087  V  S  S  S  A  T  Q  Y  G  A  H  E  Q  T  H  A  M  Y  A  C   1106
3481  CCCAAATTACCATACAACAAGGAGACAAGCCCCTTCTTTTCTACTTTGCCATTTCCACGGGC 3540
1107  P  K  L  P  Y  N  K  E  T  S  P  S  F  Y  F  A  I  S  T  G   1126
3541  TCCCTTGCTCAGCAGTATGCGCACCCCAACGCTCTGGACAGCAGCAAACATGGTGGAAGTCATCCTGCA 3600
1127  S  L  A  Q  Q  Y  A  H  P  N  A  T  L  H  P  H  T  P  H  P   1146
3601  CAGCCTTCAGCTACACCCCACTGGACAGCAGCAAAGCCAACATGGTGGAAGTCATCCTGCA 3660
1147  Q  P  S  A  T  P  T  G  Q  Q  Q  S  Q  H  G  G  S  H  P  A   1166
3661  CCCAGTCCTGTTCAGCACCATCAGCAGGCCGCCACCAGCGCCTCTCCATCTGGCCAGTCCA 3720
```

FIG. 6E

```
1167  P  S  P  V  Q  H  H  Q  H  Q  A  A  Q  A  L  H  L  A  S  P       1186
3721  CAGCAGCAGTCAGCCATTACCACGCGGGGCTTGCGCCAACTCCACCCTCCATGACACCT       3780
1187  Q  Q  Q  S  A  I  Y  H  A  G  L  A  P  T  P  P  S  M  T  P       1206
3781  GCCTCCAACACGCAGTCGCCACAGAATAGTTTCCCAGCAGCAACAGACTGTCTTTACG        3840
1207  A  S  N  T  Q  S  P  Q  N  S  F  P  A  A  Q  Q  T  V  F  T       1226
3841  ATCCATCCTTCTCAGTTCAGCCGGCGTATACCAACCCACCCACATGGCCCACGTACCT        3900
1227  I  H  P  S  H  V  Q  P  A  Y  T  N  P  P  H  M  A  H  V  P       1246
3901  CAGGCTCATGTACAGTCAGGAATGGTTCCTCATCCAACTGCCCATGGCCAATGATG          3960
1247  Q  A  H  V  Q  S  G  M  V  P  S  H  P  T  A  H  A  P  M  M       1266
3961  CTAATGACGACACAGACAGTCTCTGACAACAGAGCCGTCCCCAGGCGCCTCAAAGTGCACTACAG 4020
1267  L  M  T  T  Q  P  P  G  G  P  Q  A  A  L  A  Q  S  A  L  Q       1286
4021  CCCATTCCAGTCTGCTGACAACAGCGCCATTCCCTATATGACGACCCTTCAGTACAAGCC      4080
1287  P  I  P  V  S  T  T  A  H  F  P  Y  M  T  H  P  S  V  Q  A       1306
4081  CACCACCAACAGCAGTCAGTTGTAAGGCTGCCCTGGAGGAACCGAAAGGCCAAATTCCCTCCTC  4140
1307  H  H  Q  Q  L  *                                                 1326
4141  CCTTCTACTGCTTCTACCAACTGGAAGCACAGAAAACTAGAATTTCATTTATTTGTTTT       4200
4201  TAAAATATATATATGTTGATTTCTTGTAACATCAATAGGAAATGCTAACAGTTCACTTGCAG   4260
4261  TGGAAGATACTTGGACCGAGTAGAGCATTTAGGAACTTGGGGCTATTCCATAATTCCA       4320
4321  TATGCTGTTTCAGATGTCCCGCAGTACCCCAGTCTGCTTGCCGAAACTGGAAGTTATTT      4380
4381  ATTTTTAATAACCCTTGAAAGTCATGAACACATCAGTAGCAAAAGAAGTAACAAGAGT       4440
4441  GATTCTTGCTATTACTGCTAAAAAAAAAAAAAAAAAAAA 4481
```

FIG. 6F

```
                     1                                                                    50
Ataxin-2         VYGPLTMSLK PQQQQQQQQQ QQQQQQQQQQ QQQPPPAAAN VRKPGGSGLL
Mouse Ataxin-2   HEGPLTMSLK PQPQ...... .......... ....PPAPAT GRKPGG.GLL
A2RP             .........LA PQPPPPQQHQ ER........ .......... ..........
Consensus        ---------- -L-----PQ- ---------- ---------- ----------

51                                                                  100
Ataxin-2         ASPAAAPSPS SSSVSSSSAT APSSVVA... ATSGGGRPGL GRGRNSNKGL
Mouse Ataxin-2   SSPGAAP.AS AAVTSASVVP APAAPVASSS AAAGGGRPGL GRGRNSSKGL
A2RP             ..PGAAAIGS A......... .......... .RGQSTGKGP ..........
Consensus        --P-AA---S ---------- ---------- --RG------ -KG-------

101                                                                 150
Ataxin-2         PQSTISFDGI YANMRMVHIL TSVVGSKCEV QVKNGGIYEG VFKTYSPKCD
Mouse Ataxin-2   PQPTISFDGI YANVRMVHIL TSVVGSKCEV QVKNGGIYEG VFKTYSPKCD
A2RP             PQSPV.FEGV YNNSRMLHFL TAVVGSTCDV KVKNGTTYEG IFKTLSSKFE
Consensus        PQ-----F-G- Y-N-RM-H-L T-VVGS-C-V -VKNG--YEG -FKT-S-K--

151                                                                 200
Ataxin-2         LVLDAAHEKS TESSSGPKRE EIMESILFKC SDFVVVQFKD MDSSYAKRDA
Mouse Ataxin-2   LVLDAAHEKS TESSSGPKRE EIMESVLFKC SDFVVVQFKD TDSSYARRDA
A2RP             LAVDAVHRKA SEPAGGPRRE DIVDTMVFKP SDVMLVHFRN VDFNYATKDK
Consensus        L--DA-H-K- -E---GP-RE -I-----FK- SD---V-F-- -D--YA--D-
```

FIG. 7A

```
              201                                                          250
Ataxin-2        FTDSAIS..A KVNGEHKEKD LEPWDAGELT ANEELEALEN DVSNGWDPND
Mouse Ataxin-2  FTDSALS..A KVNGEHKEKD LEPWDAGELT ASEELE.LEN DVSNGWDPND
A2RP            FTDSAIAMNS KVNGEHKEKV LQRWEGGD.S NSDDYD.LES DMSNGWDPNE
Consensus       FTDSA----- KVNGEHKEK- L--W--G--- ------LE-  D-SNGWDPN- 251                                                          300
Ataxin-2        MFRYNEENYG VVSTYDSSLS SYTVPLERDN SEEFLKREAR ANQLAEEIES
Mouse Ataxin-2  MFRYNEENYG VVSTYDSSLS SYTVPLERDN SEEFLKREAR ANQLAEEIES
A2RP            MFKFNEENYG VKTTYDSSLS SYTVPLEKDN SEEFRQRELR AAQLAREIES
Consensus       MF--NEENYG V--TYDSSLS SYTVPLE-DN SEEF--RE-R A-QLA-EIES 301                                                          350
Ataxin-2        SAQYKARVAL ENDD.RSEEE KYTAVQRNSS EREGHSINTR ENKYIPPGQR
Mouse Ataxin-2  SAQYKARVAL ENDD.RSEEE KYTAVQRNCS DREGHGPNTR DNKYIPPGQR
A2RP            SPQYRLRIAM ENDDGRTEEE KHSAVQRQGS GRESPSLASR EGKYIP....
Consensus       S-QY-R-A-  ENDD-R-EEE K--AVQR--S -RE------R  --KYIP----

351
Ataxin-2        NR
Mouse Ataxin-2  NR
A2RP            ..
Consensus       --
```

FIG. 7B

NUCLEIC ACID ENCODING SPINOCEREBELLAR ATAXIA-2 AND PRODUCTS RELATED THERETO

CROSS-REFERENCE TO RELATED APPLICATIONS

This application is a U.S. National Stage application which claims priority to International Application No. PCT/US97/07725 (filed May 8, 1997), which is a continuation-in-part of U.S. patent application Ser. No. 08/727,084 (filed Oct. 8, 1996), now abandoned, which further claims priority to provisional application Serial No. 60/017,388 (filed May 8, 1996) and 60/022,207 (filed Jul. 19, 1996), all of which are incorporated herein by reference.

BACKGROUND OF THE INVENTION

Disorders of the cerebellum and its connections are a major cause of neurologic morbidity and mortality. One of the cardinal features of lesions in these pathways is ataxia or incoordination of movements and gait. Although some of the lesions have obvious etiologies such as trauma, strokes or tumors, the etiology of many ataxias has remained difficult to define and is due to metabolic deficiencies, remote effects of cancer or genetic causes. Hereditary spinocerebellar degenerations have a prevalence of 7–20 cases per 100,000 (Filla et al., *J. of Neurology* 239(6):351–353 (1992); Polo et al., *Brain* 114 (pt2):855–866 (1991)) which equals the estimates for the prevalence of multiple sclerosis in the United States based on clinical analysis and genetic inheritance patterns several forms of ataxias are now recognized. Among the genetic causes of ataxic disorders, the autosomal dominant spinocerebellar ataxias (SCAs) have been the most difficult to classify and until recently no clues to their cause existed.

The SCAs are progressive degenerative neurological diseases of the nervous system characterized by a progressive degeneration of neurons of the cerebellar cortex. Degeneration is also seen in the deep cerebellar nuclei, brain stem, and spinal cord. Clinically, affected individuals suffer from severe ataxia and dysarthria, as well as from variable degrees of motor disturbance and neuropathy. The disease usually results in complete disability and eventually in death 10 to 30 years after onset of symptoms. The genes for SCA types 1 and 3 have been identified. Both contain CAG DNA repeats that cause the disease when expanded. However, little is known how CAG repeat expansion and consequent elongation of polyglutamine tracts translate into neurodegeneration. The identification of the SCA2 gene would provide the opportunity to study this phenomenon in a new protein system.

The significance of identifying ataxia genes goes beyond improved diagnosis for individuals, the possibility of prenatal/presymptomatic diagnosis or better classification of ataxias. Most of the genes associated with repeat expansions in the coding region including the genes for SCA1 and SCA3 are genes that show no homology to known genes. Thus, isolation of these genes will likely point to pathways leading to late-onset neurodegeneration that are novel and may have importance for other neurodegenerative diseases.

For example, it has been suggested that CAG expansion may result in increased transglutamination of proteins, a process that has also been implicated in Alzheimer's disease. The ataxias in particular offer the unique opportunity to study how different genes may either independently or through conjoined action in the same pathway produce relatively similar phenotypes in humans. Therefore, it may be possible to examine the interaction of these genes on age of onset and phenotype, and explain that part of phenotypic variability that is not explained by determining repeat expansion in the mutant allele. Cosmids and YACs have been the main tools for generating contig maps of chromosomal regions and the entire genome, respectively. Recently, novel cloning vectors (reviewed in Ioannou et al., *Nat. Genet.* 6:84–89 (1994)) have been developed that may be more stable than cosmids, while being considerable larger.

Several systems of classification have been proposed for the SCAs based on pathological, clinical or genetic criteria. However, these attempts have been hampered by the extreme variability of disease onset and clinical features within and between families. Among the dominant ataxias only Machado-Joseph disease (MJD) has been clinically defined as a separate disease based on the prominence of basal ganglia involvement. However, since phenotypic variability is remarkable in MJD pedigrees, the assignment of individual cases or small families to this category is difficult. Indeed, after identification of the MJD locus (SCA3) it has become apparent that families with a phenotype not typical of MJD, but resembling SCAs are linked to the same locus as SCA3 families.

The advent of genetic linkage analysis provided a novel means to approach classification of the SCAs. Since the late 70's it was recognized that some SCA pedigrees appeared to show linkage to the HLA locus on CHR6, while others did not. Later this locus, now called SCA1, was further defined using RFLP and microsatellite markers and was mapped centromeric to the HLA locus. After the establishment of flanking markers for the SCA1 gene it became rapidly apparent that many—if not the majority—of SCA families did not show linkage to the SCA1 locus. Recently, a second SCA locus was identified on CHR12 using a large pedigree of Cuban descent (Gispert et al., *Nat. Genet.* 4:295–299 (1993)) and in a pedigree of Southern Italian origin (Pulst et al., *Nat. Genet.* 5:8–10 (1993)). At the same time a third locus for Machado-Joseph disease and other pedigrees with an SCA phenotype was identified on CHR14 (Takiyama et al, *Nat. Genet.* 4:300–304 (1993)). Recently, SCA4 was mapped to CHR16 and SCA5 to CHR11 (Ranum et al., *Nat. Genet.* 8:N3:280–284 (1994)).

Two of the SCA genes have been identified, one by a positional cloning approach, the other by a cDNA based approach. The SCA1 gene was identified by screening a cosmid contig covering the region between the two flanking markers D6S274 and D6S89 for cosmids containing CAG repeats. A CAG repeat was isolated, and shown to be expanded in affected individuals (Orr et al., *Nat. Genet.* 4:221–226 (1993); see Table 1). The number of CAG repeats are inversely correlated with the age of onset. Recently, the complete coding sequence for the SCA1 gene has been determined. The gene does not appear to be homologous to other known genes. Despite the tissue specific effects of the mutation, SCA1 transcripts are ubiquitously expressed. By RT-PCR analysis, normal and mutated transcripts are found in tissues indicating that repeat expansion does not interfere with transcription.

The SCA3 or MJD gene was identified after several CAG containing cDNA clones had been isolated from a brain cDNA library (Kawaguchi et al., *Nat. Genet.* 8:221–227 (1994)). One of these mapped to CHR 14q32.1, the region previously identified by genetic linkage analysis to contain the SCA3 gene. The CAG repeat was expanded in affected individuals, but appears to show greater meiotic stability than other CAG repeats. The SCA3 gene has no homology to other known genes or motif structures, but related sequences were identified on CHR 8q23, 14q21, and Xp22.1.

Although not an SCA gene in the strict sense, CAG expansion in the gene causing dentatorubral-pallidoluysian atrophy (DRPLA) may also lead to degeneration of cerebellar neurons. This gene was identified by searching published brain cDNA sequences for the presence of CAG repeats. A cDNA mapped to CHR12p was found to harbor a CAG repeat which was expanded in DRPLA patients (Koide et al., Nat. Genet. 6:9–13 (1994); Nagafuchi et al., Nat. Genet. 6:14–18 (1994)). The gene which has no known homologies is ubiquitously expressed. SCA families linked to markers on CHR 12 have been described in several ethnic backgrounds. The largest ones are of Cuban ancestry (H pedigree), French-Canadian and Austrian ancestry (SAK and GK pedigrees, Lopes-Cendes et al., Am. J. Hum. Genet. 54:774–781 (1994)) and Italian descent (FS pedigree, Pulst et al., (1993)). A smaller Tunisian pedigree has been described as well (Belal et al., Neurology 44:1423–1426 (1994)). Although all pedigrees have cases with early onset in recent generations, a formal age of onset analysis has only been performed for the FS pedigree. This analysis indicated clear evidence of anticipation (Pulst et al., (1993)).

The phenomenon of unstable DNA repeats raises many fascinating issues. For example, in 1991, La Spada et al. identified a polymorphic CAG repeat in the androgen receptor gene on the X chromosome that was greatly expanded in individuals with spinobulbar muscular atrophy (SBMA, Kennedy syndrome). In short succession, a total of ten diseases were found to be caused by trinucleotide repeat (TNR) expansion (Table 1). Although several unifying concepts emerge from the comparison of diseases caused by TNR expansion, important differences can be recognized as well.

Common to all diseases is a highly polymorphic number of repeats on normal chromosomes. If the repeat number reaches allele sizes in between normal and disease alleles—termed premutations—the repeat becomes unstable and may expand to the size associated with the disease state. Large number repeats have the tendency to expand further, although decreases in size are occasionally seen (Bruner et al., New Engl. J. Med. 328:476–480 (1993); reviewed in Brook, Nat. Genet. 3:279–152 (1993); Mandel, Nat. Genet. 4:8–9 (1993)).

TABLE 1

Characteristics of diseases caused by TNR expansion

| Disease | Type of repeat | Location of repeat | Number of repeats in normal alleles | Number of repeats in disease alleles |
| --- | --- | --- | --- | --- |
| Fragile X syndrome | CGG | 5' untr. | 5–54 | 200–200 |
| FRAXE | GCC | unknown | 6–25 | 200–80 |
| FRAXF | GCC | unknown | 6–29 | 300–500 |
| FRA16A | GCC | unknown | 16–49 | 1000–20000 |
| Myotonic dystrophy | CTG | 3' untr. | 5–35 | 100–200 |
| SBMA | CAG | coding | 11–31 | 40–62 |
| Huntington disease | CAG | coding | 15–38 | 38–120 |
| CA 1 | CAG | coding | 25–36 | 43–81 |
| DRPLA | CAG | coding | 7–26 | 49–75 |
| MJD (SCA3) | CAG | coding | 13–36 | 68–79 |

TNR expansion may be a common form of human mutagenesis. Especially if expansion is not restricted to pure CAG and CCG repeats, the number of genes predisposed to expansion may be quite large. Three diseases with cerebellar degeneration, SCA1, DRPLA, and SCA3 are caused by expansion of a CAG repeat. In these diseases clear evidence of anticipation was lacking, although very early onset cases in some families had raised this question. However, as described in Pulst et al. (1993) strong evidence for anticipation was identified in the FS pedigree with SCA2. Thus, there is a need in the art to identify the location and nucleic acid structure of the SCA2 gene.

SUMMARY OF THE INVENTION

The present invention provides isolated nucleic acids encoding the human SCA2 protein and isolated proteins encoded thereby. Further provided are vectors containing invention nucleic acids, probes that hybridize thereto, host cells transformed therewith, antisense oligonucleotides thereto and compositions containing, antibodies that specifically bind to invention polypeptides and compositions containing, as well as transgenic non-human mammals that express the invention protein. In addition, methods for diagnosing spinocerebellar Ataxia Type 2, or a presisposition thereto, are provided.

BRIEF DESCRIPTION OF THE FIGURES

FIG. 2 shows the nucleic acid sequence (SEQ ID NO:1) of plasmid PL65I22B for genomic DNA encoding the expansion of the CAG repeat in individuals with SCA2. Nucleotides 1–499 of FIG. 2 correspond to cDNA nucleotides 392–890 of FIG. 6 (SEQ ID NO:2). The locations of primers SCA2-A and SCA2-B are indicated by arrows. The location of a predicted splice site is indicated by a vertical arrow-between nucleotides 499 and 500 (also compare with FIG. 6).

FIG. 6 shows the composite cDNA sequence (SEQ ID NO:2) obtained from assembly of the partially overlapping cDNA clones shown in FIG. 5. The predicted SCA2 protein product (SEQ ID NO:3) is shown below the DNA sequence. The stop codon for the SCA2 cDNA is indicated by *. The locations of primers SCA2-A, SCA2-B, and SCA2-B14 are indicated by horizontal arrows. The splice site between primers SCA2-B and SCA2-B14 is indicated by a vertical arrow.

FIG. 7 shows s partial amino acid sequence alignment comparison of ataxin-2 protein (SEQ ID NO:16), the ataxin-2 related protein (A2RP) (SEQ ID NO:18), and the mouse SCA2 homologue (SEQ ID NO:17) in the region of strongest homology. Codon 1 corresponds to codon 155 in FIG. 6 (SEQ ID NO:3).

DETAILED DESCRIPTION OF THE INVENTION

Figure 1:
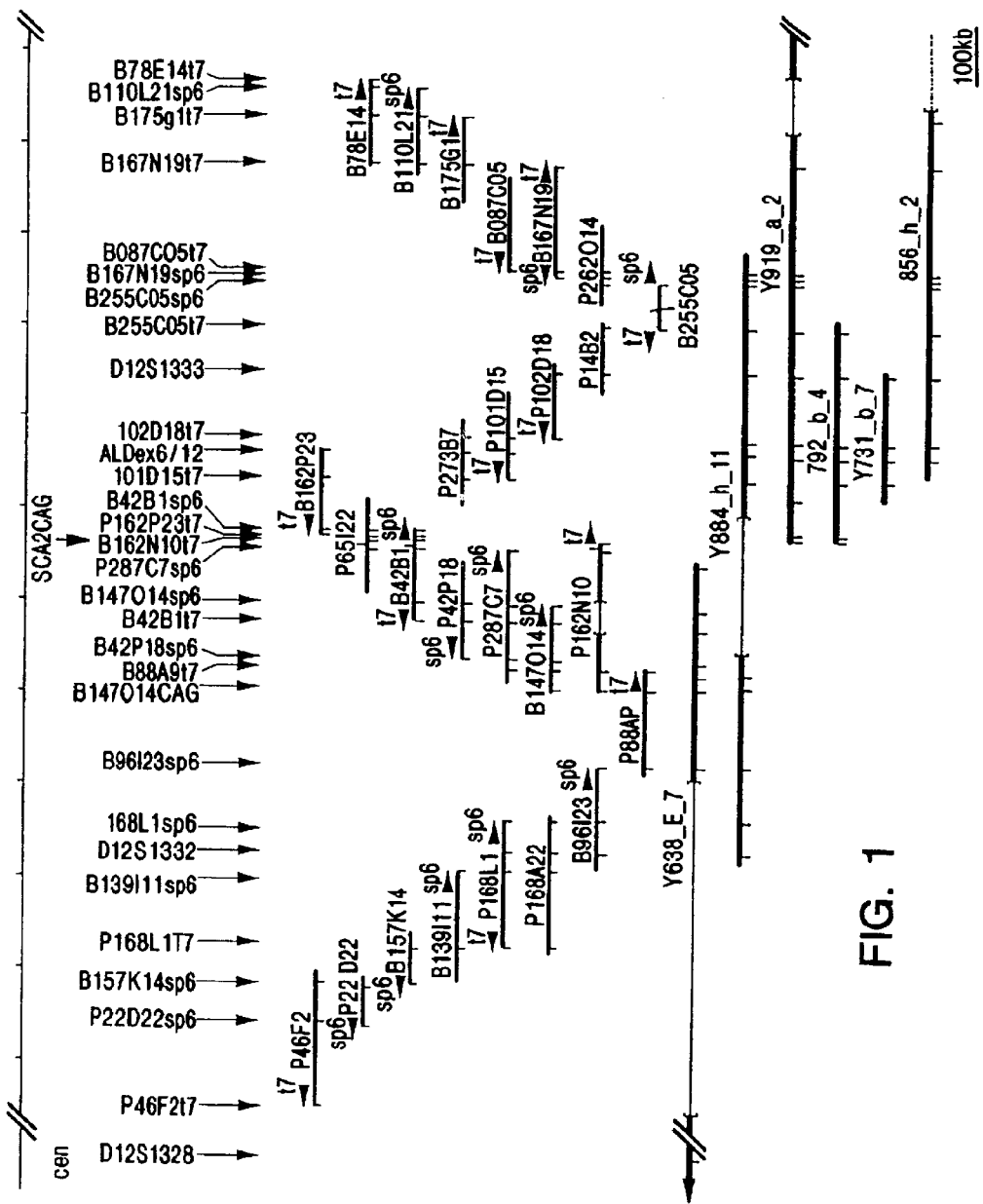
FIG. 1 shows a physical map of the SCA2 region. The location of D12S1328 centromeric and D12S1329 telomeric of the contig are indicated. As indicated by double forward slashes, the map is not drawn to scale between D12S1328 and P46F2t7, and between B78E14t7 and D12S1329. YAC, PAC and BAC clones are prefixed with 'Y', 'P', and 'B' respectively. Clones positive for a specific STS by PCR analysis are indicated by vertical lines. Solid arrows indicate end-STSs from the clone under the symbol. Sizes of all clones are shown to scale. The chimeric part of YAC clone 856_h_2(1,100 kb) is indicated by a dashed arrow. Interstitial deletions in YACs or PACs are indicated by thin lines in brackets. The extent of the deletion in YAC Y638_e_7 is not precisely known.

The hereditary ataxias are a complex group of neurodegenerative disorders all characterized by varying abnormalities of balance attributed to dysfunction or pathology of the cerebellum and cerebellar pathways. In many of these disorders, dysfunction or structural abnormalities extend beyond the cerebellum, and may involve basal ganglia function, oculo-motor disorders and neuropathy. Among the inherited ataxias, the classification of dominant adult onset ataxias is particularly controversial with regard to nomenclature, associated findings and pathology. The dominant spinocerebellar ataxias (SCAs) represent a phenotypically heterogeneous group of disorders with a prevalence of familial cases of approximately 1 per 100,000. This group of disorders is also designated as olivo-ponto-cerebellar atrophies (OPCAs), although this term is too restrictive a pathological label.

The high phenotypic variability within single SCA pedigrees has made clinical classification of different forms of ataxia difficult. The gene causing SCA1 has been identified on CHR 6p and the SCA3 gene has been identified on CHR 14q. These diseases are caused by expansion of a CAG repeat in the coding region of the genes. However, many SCA pedigrees do not show linkage to CHR 6p or CHR 14q, confirming the presence of non-allelic heterogeneity. Subsequent genetic linkage studies have led to the identification of SCA loci on CHR12 and some families do not show linkage to either of the above three chromosomal regions.

Described in the instant specification is the construction of the BAC (Bacterial Artificial Chromosome) Shizuya et al., *Proc. Natl. Acad. Sci. USA* 89:8794–8797 (1992) contig and PAC (P1 Artificial Chromosome) of the SCA2 region and the isolation of a novel SCA2 gene from this contiguous map unit using a technique that screens for the presence of DNA trinucleotide repeats.

Sequence analysis of the DNA sequence flanking the CAG repeat revealed an open reading frame of 317 base pairs (FIG. 2). A homology search of the amino acid sequence of this open reading frame (ORF) with genes registered in Genbank/EMBL and search of the TIGR database showed no homologous proteins or homologous genomic DNA sequences. Using reverse-transcribed PCR (polymerase chain reaction) with primers SCA1-A and SCA1-B, the genomic sequence containing the CAG repeat was shown to be expressed into mRNA. Subsequently, cDNA encoding human and mouse SCA2 has been isolated as described hereinafter in Examples 4 and 7, respectively.

Accordingly, the present invention provides isolated nucleic acids, which encode a novel mammalian SCA2 protein, and fragments thereof. Such nucleic acids can be obtained, for example, from human chromosome 12, specifically at the q24.1 locus, which is the site of mutation(s) that cause SCA2.

The term "nucleic acids" (also referred to as polynucleotides) encompasses RNA as well as single and double-stranded DNA and cDNA. As used herein, the phrase "isolated" means a nucleic acid that is in a form that does not occur in nature. One means of isolating a nucleic acid encoding an SCA2 polypeptide is to probe a mammalian genomic library with a natural or artificially designed DNA probe using methods well known in the art. DNA probes derived from the SCA2 gene are particularly useful for this purpose. DNA and cDNA molecules that encode SCA2 polypeptides can be used to obtain complementary genomic DNA, cDNA or RNA from human, mammalian (e.g., mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an SCA2 polypeptide. Such invention nucleic acids may include, but are not limited to, nucleic acids having substantially the same nucleotide sequence as nucleotides 163–4098 set forth in SEQ ID NO:2 (FIG. 6), or at least nucleotides 163–657 or nucleotides 724–4098 of SEQ ID NO:2; or nucleotides 50–3454 of SEQ ID NO:4. In a preferred embodiment, invention nucleic acids include the same nucleotide sequence as nucleotides 163–4098 of SEQ ID NO:2, or include the same nucleotide sequence as nucleotides 50–3454 of SEQ ID NO:4.

As employed herein, the phrase "substantially the same nucleotide sequence" refers to DNA having sufficient homology to the reference polynucleotide, such that it will hybridize to the reference nucleotide under typical moderate stringency conditions. In one embodiment, nucleic acid molecules having substantially the same nucleotide sequence as the reference nucleotide sequence encodes substantially the same amino acid sequence as that of either SEQ ID NO:3, or SEQ ID NO:5. In another embodiment, DNA having "substantially the same nucleotide sequence" as the reference nucleotide sequence has at least 60% homology with respect to the reference nucleotide sequence. DNA having at least 70%, more preferably 80%, yet more preferably 90%, homology to the reference nucleotide sequence is preferred.

This invention also encompasses nucleic acids which differ from the nucleic acids shown in SEQ ID NO:1, SEQ ID NO:2, or SEQ ID NO:4, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding SCA2 polypeptides that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in SEQ ID NO:3 (FIG. 6), or SEQ ID NO:5.

As employed herein, the term "substantially the same amino acid sequence" refers to amino acid sequences having at least about 70% identity with respect to the reference amino acid sequence, and retaining comparable functional and biological properties characteristic of the protein defined by the reference amino acid sequence. Preferably, proteins having "substantially the same amino acid sequence" will have at least about 80%, more preferably 90% amino acid identity with respect to the reference amino acid sequence (SEQ ID NO:3 or SEQ ID NO:5); with greater than about 95% amino acid sequence identity being especially preferred.

Alternatively, preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NO:1, SEQ ID NO:2 (FIG. 6) or SEQ ID NO:4.

Stringency of hybridization, as used herein, refers to conditions under which polynucleotide hybrids are stable. As known to those of skill in the art, the stability of hybrids is a function of sodium ion concentration and temperature (See, for example, Sambrook et al., *Molecular Cloning: A Laboratory Manual 2d Ed.* (Cold Spring Harbor Laboratory, (1989); incorporated herein by reference). Stringency levels used to hybridize a given probe with target-DNA can be readily varied by those of skill in the art.

As used herein, the phrase "moderately stringent" hybridization refers to conditions that permit target-DNA to bind a complementary nucleic acid that has about 60%, preferably about 75%, more preferably about 85%, homology (i.e., identity) to the target DNA; with greater than about 90% homology to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C. Denhart's solution and SSPE (see, e.g., Sambrook et al., *Molecular Cloning, A Laboratory Manual,* Cold Spring Harbor Laboratory Press, (1989)) are well known to those of skill in the art as are other suitable hybridization buffers.

Also provided are isolated SCA2 peptides, polypeptide (s) and/or protein(s), or fragments thereof, encoded by the invention nucleic acids.

As used herein, the term "isolated" means a protein molecule free of cellular components and/or contaminants normally associated with a native in vivo environment. Invention polypeptides and/or proteins include any isolated natural occurring allelic variant, as well as recombinant forms thereof. The SCA2 polypeptides can be isolated using various methods well known to a person of skill in the art. The methods available for the isolation and purification of invention proteins include, precipitation, gel filtration, ion-exchange, reverse-phase and affinity chromatography. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., supra., 1989).

An example of the means for preparing the invention polypeptide(s) is to express nucleic acids encoding the SCA2 in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors, described below in more detail. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

As used herein, the phrase "SCA2" refers to substantially pure native SCA2 protein, or recombinantly expressed/ produced (i.e., isolated or substantially pure) proteins, including variants thereof encoded by mRNA generated by alternative splicing of a primary transcript, and further including fragments thereof which retain native biological activity. Preferred invention polypeptides are those that contain substantially the same amino acid sequence set forth in SEQ ID NO:3 (FIG. 6), or at least amino acids 1–165 or amino acids 188–1312 of SEQ ID NO:3, or include substantially the same amino acid sequence set forth in SEQ ID NO:5. As used herein, the phrase "functional polypeptide" means a SCA2 that can produce an anti-SCA2 antibody that binds to the native SCA2 protein or to the amino acid sequence set forth in SEQ ID NO:3 (FIG. 6), or SEQ ID NO:5. In a preferred embodiment, invention polypeptides include the same amino acid sequence as set forth in SEQ ID NO:3 or SEQ ID NO:5.

Modification of the invention nucleic acids, polypeptides or proteins with the following phrases: "recombinantly expressed/produced", "isolated", or "substantially pure", encompasses nucleic acids, peptides, polypeptides or proteins that have been produced in such form by the hand of man, and are thus separated from their native in vivo cellular environment. As a result of this human intervention, the recombinant nucleic acids, polypeptides and proteins of the invention are useful in ways that the corresponding naturally occurring molecules are not, such as identification of selective drugs or compounds.

Sequences having "substantially the same sequence" homology are intended to refer to nucleotide sequences that share at least about 75%, preferably about 80%, yet more preferably about 90% identity with invention nucleic acids; and amino acid sequences that typically share at least about 75%, preferably about 85%, yet more preferably about 95% amino acid identity with invention polypeptides. It is recognized, however, that polypeptides or nucleic acids containing less than the above-described levels of homology arising as splice variants or that are modified by conservative amino acid substitutions, or by substitution of degenerate codons are also encompassed within the scope of the present invention.

The present invention provides the isolated polynucleotide encoding SCA2 operatively linked to a promoter of RNA transcription, as well as other regulatory sequences. As used herein, the phrase "operatively linked" refers to the functional relationship of the polynucleotide with regulatory and effector sequences of nucleotides, such as promoters, enhancers, transcriptional and translational stop sites, and other signal sequences. For example, operative linkage of a polynucleotide to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, and the like.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. (See, for example, Kozak, *J. Biol. Chem.* 266:19867 (1991)). Similarly, alternative codons, encoding the same amino acid, can be substituted for coding sequences of the SCA2 polypeptide in order to enhance transcription (e.g., the codon preference of the host cell can be adopted, the presence of G-C rich domains can be reduced, and the like).

Also provided are vectors comprising invention nucleic acids. Examples of vectors are viruses, such as baculoviruses and retroviruses, bacteriophages, cosmids, plasmids and other recombination vehicles typically used in the art. Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA.

Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Further provided are vectors comprising nucleic acids encoding SCA2 polypeptides, adapted for expression in a bacterial cell, a yeast cell, an amphibian cell (i.e., oocyte), a mammalian cell and other animal cells. The vectors additionally comprise the regulatory elements necessary for expression of the nucleic acid in the bacterial, yeast, amphibian, mammalian or animal cells so located relative to the nucleic acid encoding SCA2 polypeptide as to permit expression thereof.

As used herein, "expression" refers to the process by which nucleic acids are transcribed into mRNA and translated into peptides, polypeptides, or proteins. If the nucleic acid is derived from genomic DNA, expression may include splicing of the mRNA, if an appropriate eucaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. supra). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention polypeptide.

The present invention provides transformed host cells that recombinantly express SCA2 polypeptides. An example of a transformed host cell is a mammalian cell comprising a plasmid adapted for expression in a mammalian cell. The plasmid contains nucleic acid encoding an SCA2 polypeptide and the regulatory elements necessary for expression of invention proteins. Various mammalian cells may be utilized as hosts, including, for example, mouse fibroblast cell NIH3T3, CHO cells, HeLa cells, Ltk– cells, etc. Expression plasmids such as those described supra can be used to transfect mammalian cells by methods well known in the art such as, for example, calcium phosphate precipitation, DEAE-dextran, electroporation, microinjection or lipofection.

The present invention provides nucleic acid probes comprising nucleotide sequences capable of specifically hybridizing with sequences included within nucleic acids encoding SCA2 polypeptides, for example, a coding sequence included within the nucleotide sequence shown in SEQ ID NO:2 (FIG. 6), or SEQ ID NO:4. In a preferred embodiment, the probe is derived from the nucleic acid sequence set forth in SEQ. ID NO:2, or at least nucleotides 163–657 or nucleotides 724–4098 of SEQ ID NO:2; or SEQ ID NO:4. Preferred regions from which to construct probes include 5' and/or 3' coding sequences, sequences within the ORF, and the like. Full-length or fragments of cDNA clones encoding SCA2 can also be used as probes for the detection and isolation of related genes. As used herein, an invention "probe" or invention oligonucleotide is a single-stranded DNA or RNA that has a sequence of nucleotides that includes at least about 15 contiguous bases up to the full length coding region of SEQ ID NO:2 or SEQ ID NO:4. Preferably an invention probe is at least about 30 contiguous bases, more preferably at least about 50, yet more preferably at least about 100, with about 300 contiguous bases up to the full length coding region of SEQ ID NO:2 and SEQ ID NO:4 being especially preferred. When fragments are used as probes, preferably the cDNA sequences will be from the carboxyl end-encoding portion of the cDNA, and most preferably will include predicted transmembrane domain-encoding portions of the cDNA sequence. Transmembrane domain regions can be predicted based on hydropathy analysis of the deduced amino acid sequence using, for example, the method of Kyte and Doolittle, *J. Mol. Biol.* 157:105 (1982).

As used herein, the phrase "specifically hybridizing" encompasses the ability of a polynucleotide to recognize a sequence of nucleic acids that are complementary thereto and to form double-helical segments via hydrogen bonding between complementary base pairs. Nucleic acid probe technology is well known to those skilled in the art who will readily appreciate that such probes may vary greatly in length and may be labeled with a detectable agent, such as a radioisotope, a fluorescent dye, and the like, to facilitate detection of the probe. Invention probes are useful to detect the presence of nucleic acids encoding the SCA2 polypeptide. For example, the probes can be used for in situ hybridizations in order to locate biological tissues in which the invention gene is expressed. Additionally, synthesized oligonucleotides complementary to the nucleic acids of a nucleotide sequence encoding SCA2 polypeptide are useful as probes for detecting the invention genes, their associated mRNA, or for the isolation of related genes using homology screening of genomic or cDNA libraries, or by using amplification techniques well known to one of skill in the art.

Also provided are antisense oligonucleotides having a sequence capable of binding specifically with any portion of an mRNA that encodes SCA2 polypeptides so as to prevent or inhibit translation of the mRNA. The antisense oligonucleotide may have a sequence capable of binding specifically with any portion of the sequence of the cDNA encoding SCA2 polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of SCA2 polypeptides by passing through a cell membrane and binding specifically with mRNA encoding SCA2 polypeptides so as to prevent translation and an acceptable hydrophobic carrier capable of passing through a cell membrane are also provided herein. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions are useful to inhibit translation of mRNA encoding invention polypeptides. Synthetic oligonucleotides, or other antisense chemical structures are designed to bind to mRNA encoding SCA2 polypeptides and inhibit translation of mRNA and are useful as compositions to inhibit expression of SCA2 associated genes in a tissue sample or in a subject.

In accordance with another embodiment of the invention, kits for detecting mutations and aneuploidies in chromosome 12 at locus q24.1 comprising at least one invention probe or antisense nucleotide.

The present invention provides means to modulate levels of expression of SCA2 polypeptides by employing synthetic antisense oligonucleotide compositions (hereinafter SAOC) which inhibit translation of mRNA encoding these polypeptides. Synthetic oligonucleotides, or other antisense chemical structures designed to recognize and selectively bind to mRNA, are constructed to be complementary to portions of the SCA2 coding strand or nucleotide sequences shown in SEQ ID NO:2, or SEQ ID NO:4. The SAOC is designed to be stable in the blood stream for administration to a subject by injection, or in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained within the sequence shown in SEQ ID NO:2, or SEQ ID NO:4. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIPS*, 10:435 (1989) and Weintraub, *Sci. American*, January (1990), pp.40; both incorporated herein by reference).

The present invention also provides compositions containing an acceptable carrier and any of an isolated, purified SCA2 polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

Further provided are anti-SCA2 antibodies having specific reactivity with SCA2 polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies.

Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., Trends Pharmacol. Sci. 12:338 (1991); Ausubel et al., Current Protocols in Molecular Biology (John Wiley and Sons, NY (1989) which are incorporated herein by reference).

Invention antibodies also can be used to isolate invention polypeptides. Additionally the antibodies are useful for detecting the presence of invention polypeptides, as well as analysis of chromosome localization, and structural as well as functional domains. Methods for detecting the presence of SCA2 polypeptides on the surface of a cell comprise contacting the cell with an antibody that specifically binds to SCA2 polypeptides, under conditions permitting binding of the antibody to the polypeptides, detecting the presence of the antibody bound to the cell, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target SCA2 polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Further, invention antibodies can be used to modulate the activity of the SCA2 polypeptide in living animals, in humans, or in biological tissues or fluids isolated therefrom. Accordingly, compositions comprising a carrier and an amount of an antibody having specificity for SCA2 polypeptides effective to block binding of naturally occurring ligands to invention polypeptides. A monoclonal antibody directed to an epitope of SCA2 polypeptide molecules present on the surface of a cell and having an amino acid sequence substantially the same as an amino acid sequence for a cell surface epitope of an SCA2 polypeptide shown in SEQ ID NO:3, or SEQ ID NO:5, can be useful for this purpose.

The present invention further provides transgenic non-human mammals that are capable of expressing nucleic acids encoding SCA2 polypeptides. Also provided are transgenic non-human mammals capable of expressing nucleic acids encoding SCA2 polypeptides so mutated as to be incapable of normal activity, i.e., do not express native SCA2. The present invention also provides transgenic non-human mammals having a genome comprising antisense nucleic acids complementary to nucleic acids encoding SCA2 polypeptides so placed as to be transcribed into antisense mRNA complementary to mRNA encoding SCA2 polypeptides, which hybridizes thereto and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO:2, or SEQ ID NO:4. An example of a non-human transgenic mammal is a transgenic mouse. Examples of tissue specificity-determining elements are the metallothionein promoter and the L7 promoter.

Animal model systems which elucidate the physiological and behavioral roles of SCA2 polypeptides are produced by creating transgenic animals in which the expression of the SCA2 polypeptide is altered using a variety of techniques. Examples of such techniques include the insertion of normal or mutant versions of nucleic acids encoding an SCA2 polypeptide by microinjection, retroviral infection or other means well known to those skilled in the art, into appropriate fertilized embryos to produce a transgenic animal. (See, for example, Hogan et al., Manipulating the Mouse Embryo: A Laboratory Manual (Cold Spring Harbor Laboratory, (1986)).

Another technique, homologous recombination of mutant or normal versions of these genes with the native gene locus in transgenic animals, may be used to alter the regulation of expression or the structure of SCA2 polypeptides (see, Capecchi et al., Science 244:1288 (1989); Zimmer et al., Nature 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of SCA2 polypeptides.

In contrast to homologous recombination, microinjection adds genes to the host genome, without removing host genes. Microinjection can produce a transgenic animal that is capable of expressing both endogenous and exogenous SCA2 protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of polypeptides, peptides or proteins.

In accordance with still another embodiment of the present invention, there is provided a method for identifying compounds which bind to SCA2 polypeptides. The invention proteins may be employed in a competitive binding assay. Such an assay can accommodate the rapid screening of a large number of compounds to determine which compounds, if any, are capable of binding to SCA2 proteins.

Subsequently, more detailed assays can be carried out with those compounds found to bind, to further determine whether such compounds act as modulators, agonists or antagonists of invention proteins.

In another embodiment of the invention, there is provided a bioassay for identifying compounds which modulate the activity of invention polypeptides. According to this method, invention polypeptides are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for SCA2 polypeptides.

In accordance with another embodiment of the present invention, transformed host cells that recombinantly express invention polypeptides can be contacted with a test compound, and the modulating effect(s) thereof can then be evaluated by comparing the SCA2-mediated response (via reporter gene expression) in the presence and absence of test compound, or by comparing the response of test cells or control cells (i.e., cells that do not express SCA2 polypeptides), to the presence of the compound.

As used herein, a compound or a signal that "modulates the activity" of invention polypeptides refers to a compound or a signal that alters the activity of SCA2 polypeptides so that the activity of the invention polypeptide is different in the presence of the compound or signal than in the absence of the compound or signal. In particular, such compounds or signals include agonists and antagonists. An agonist encompasses a compound or a signal that activates SCA2 protein expression. Alternatively, an antagonist includes a compound or signal that interferes with SCA2 protein expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate SCA2 activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of SCA2 polypeptides can be modulated by contacting the polypeptides with an effective amount of at least one compound identified by the above-described bioassays.

In accordance with another embodiment of the present invention, there are provided methods for diagnosing spinocerebellar Ataxia Type 2, said method comprising:

detecting, in said subject, a genomic or transcribed mRNA sequence having an expanded CAG repeat at a location corresponding to between nucleotides 657 and 724 of SEQ ID NO:2 (FIG. 6).

The number of CAG repeats required to indicate spinocerebellar Ataxia Type 2 is substantially above normal, preferably at least about 10–15 CAG repeats above normal, with at least 13 CAG repeats above normal being especially preferred. A normal amount of CAG repeats in the SCA2 gene (SEQ ID NO:2) has been found to be about 22, while 23 CAG repeats is occasionally observed. Thus, in a preferred diagnostic method, at least about 35 CAG repeats are detected between nucleotides 657 and 724 of SEQ ID NO:2 (FIG. 6), with the detection of 37 CAG repeats being especially preferred.

Although expansion of trinucleotide repeats is now recognized as an important mutational mechanism in humans and SCA2 represents the 6th disease in which expansion of a CAG trinucleotide repeat causes disease, there are several features of the SCA2 repeat that appear to be unique. In the other five CAG expansion diseases, the CAG repeats on normal chromosomes are highly polymorphic. Multiple alleles are detected and repeat sizes on normal chromosomes range from a low of 7 repeats in DRPLA to 40 repeats in SCA3/MJD. Heterozygosity for these CAG repeats in the normal population are in the range of 0.80 and above. It has been suggested that the extended normal alleles represent founder alleles which are predisposed to expansion.

The SCA2 repeat is highly unusual, because only two alleles are observed in the-normal population. A common allele with 22 repeats is found on 92% of chromosomes, a rare second allele in 8% of chromosomes. Expansion of the SCA2 CAG repeat on disease chromosomes is relatively moderate and is in the range seen with expansions in the SBMA and Huntington's Disease (HD) genes. The lowest number of repeats causing SCA2 was 36 and the most common disease allele had 37 repeats. Disease alleles showing 36 repeats have now clearly been established for HD (Rubinsztein et al., 1996, *Am. J. Hum. Genet.,* 59:16–22), although normal elderly individuals with 36–40 repeats exist and the most common HD alleles have >40 repeats. In contrast to SCA1, where normal and disease alleles may differ by only one repeat unit, the longest normal and the shortest SCA2 disease allele are separated by 13 repeats. Once expanded on disease chromosomes, the SCA2 repeat may undergo moderate expansions.

The SCA2 repeat is contained in a novel gene which is transcribed in several tissues including non-neuronal tissues. The-gene product, ataxin-2, has a predicted molecular weight of 140 kDa which is in good agreement with the 150 kDa protein observed using a monoclonal antibody to long polyglutamine tracts. A similar pattern of nearly ubiquitous expression has been observed in the other five polyglutamine diseases. Despite the phenotypic overlap of SCA2 with SCA1 and SCA3, the SCA2 gene shows no homology to these genes.

However, ataxin-2 showed significant homologies with another protein (referred to as "A2RP"; see FIG. 7). A 42 amino acid domain was identified that was 86% identical between the two proteins. The potential functional importance of this domain was underscored by the fact that it was 100% conserved in the mouse SCA2 homologue (FIG. 7). Interestingly, the polyglutamine tract was not conserved in either protein. Since the pathogenesis of polyglutamine containing proteins is still poorly understood, the identification of functionally important domains adjacent to polyglutamine tracts may provide the potential for novel strategies to analyze the function of ataxin-2. A gain of function for the mutated ataxin-2 is supported by the fact that transcripts coding for mutated alleles are detected by RT-PCR.

Expansion of the SCA2 repeat appears to be a common cause of a dominant SCA phenotype in non-Portuguese patients. When samples from 45 families with SCA were screened, samples from 8 independent pedigrees showed expansion of the SCA2 repeat. It has been suggested that there are features specific to SCA2, but this assessment was limited to families large enough to be studied by linkage analysis. A better assessment of the range of SCA2 phenotypes is now possible due to the ability to test small families and single cases. In our patient sample, most patients had a 'typical' SCA phenotype, but some patients had been classified as having an MJD phenotype and others showed a prominent dementia.

When performing direct testing for SCA2 mutations, great caution has to be exercised when interpreting the presence of expanded SCA2 alleles on polyacrylamide gels. A variable number of unrelated PCR fragments may be seen that are in the size range of expanded SCA2 repeats. Although these bands lack the typical 'shadow' bands seen when di- or trinucleotide repeats are amplified, they may interfere with the interpretation in some samples. It is therefore recommended to confirm the presence of an expanded allele by Southern blotting and hybridization with a $(CAG)_{10}$ oligonucleotide.

In yet another embodiment of the present invention, there are provided methods for diagnosing spinocerebellar Ataxia Type 2, said method comprising:
 a) contacting nucleic acid obtained from a subject suspected of having SCA2 with primers that amplify at least a nucleic acid fragment of SEQ ID NO:2 containing nucleotides 658–723 of SEQ ID NO:2, under conditions suitable to form a detectable amplification product; and
 b) detecting an amplification product containing substantially expanded CAG repeats above normal, whereby said detection indicates that said subject has SCA2.

As indicated above, substantially expanded CAG repeats have at least about 10–15 CAG repeats above normal, with at least 13 CAG repeats above normal being especially preferred. Thus, in a preferred diagnostic method, at least about 35 CAG repeats are detected between nucleotides 657 and 724 of SEQ ID NO:2 (FIG. 6), with the detection of 37 CAG repeats being especially preferred.

In accordance with another embodiment of the present invention, there are provided diagnostic systems, preferably in kit form, comprising at least one invention nucleic acid in a suitable packaging material. In one embodiment, the diagnostic nucleic acids are derived from SEQ ID NO:2 (FIG. 6), preferably derived from nucleotides 163–657 and nucleotides 724–4098, with primers SCA2-A and SCA2-B being especially preferred. In another embodiment, the diagnostic nucleic acids are derived from SEQ ID NO:4. Invention diagnostic systems are useful for assaying for the presence or absence of the extended CAG repeat sequence between nucleotides 657 and 724 of SEQ ID NO:2 in the SCA2 gene in either genomic DNA or in transcribed nucleic acid (such as mRNA or cDNA) encoding SCA2.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular extended CAG repeat sequence between the region of genomic DNA corresponding to nucleotides 657 and 724 of SEQ ID NO:2 (FIG. 6), thereby diagnosing the presence of, or a predisposition for, spinocerebellar ataxia type 2. In addition, the packaging material contains instructions indicating how the materials within the kit are employed both to detect a particular sequence and diagnose the presence of, or a predisposition for, spinocerebellar ataxia type 2.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned. herein are incorporated in their entirety by reference thereto. The invention will now be described in greater detail by reference to the following non-limiting examples.

The invention will now be described in greater detail with reference to the following non-limiting examples.

Materials and Methods

Unless otherwise stated, the present invention was performed using standard procedures, as described, for example in Maniatis et al., *Molecular Cloning: A Laboratory Manual,* Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology,* Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987)).

Libraries

Yeast artificial chromosome (YAC) clones were obtained from the CEPH mega-YAC library and grown under standard conditions (Cohen et al., *Nature* 366:689–701 (1993)). P1 artificial chromosome (PAC) library construction. A 3X human PAC library, designated RPCI-1 (Ioannou et al., Hum. Genet. 219–220 (1994b)) was constructed as described (Ioannou et al., *Nat. Genet.* 6:84–89 (1994a)). The library was arrayed in 384 well dishes. Pools from portion of the library were screened by PCR with AFM154TC5

(D12S1333) and AFMa128yf1 (D12S1332). Subsequently, STSs generated by sequencing of clones using vector primers were used as hybridization probes to gridded colony filters of the PAC library.

YAC DNA Preparation

YAC clones were grown in selective media, pelleted and resuspended in 3 ml 0.9 M sorbitol, 0.1M EDTA pH 7.5, then incubated with 100 U of lytocase (Sigma) at 37° C. for 1 hour. After centrifugation for 5 minutes at 5,000 rpm pellets were resuspended in 3 ml 50 mM Tris pH 7.45, 20 mM EDTA three-tenth ml 10% SDS was added and the mixture was incubated at 65° C. for 30 minutes. One ml of 5 M potassium acetate was added and tubes were left on ice for 1 hour, then centrifuged at 10,000 rpm for 10 minutes. Supernatant was precipitated in 2 volumes of ethanol and pelleted at 6,000 rpm for 15 minutes. Pellets were resuspended in TE, treated with RNase and reextracted with phenol-chloroform.

Analysis by Pulsed-field Gel Electrophoresis

Agarose plugs of yeast cells containing total YAC DNA were prepared (Larin and Lehrach, Genet. Rcs. 56:203–208 (1990)) and subjected to pulsed-field gel separation on 1% SeaKem agarose gels in 0.5×TBE using the CHEF DRII Mapper (Bio-Rad). PAC and BAC clones were sized after digestion with XbaI and NotI. Gels were blotted onto Magna NT Nylon membranes using alkaline blotting, UV cross linked and baked at 80° C. for two hours. Membranes were hybridized with total human DNA, washed according to standard procedures, and exposed to Kodak XAR5 film. The sizes of individual clones were determined by comparison to their relative positions with molecular weight standards.

Analysis by Fluorescence in situ Hybridization (FISH)

PAC or BAC clones were biotinylated by nicktranslation in the presence of biotin-14-dATP using the BioNick Labeling Kit (Gibco-BRL). FISH was performed essentially as described (Korenberg et al., *Cytogenet Cell Genet.* 69:196–200 (1995)). Briefly, 400 ng of probe DNA was mixed with 8 ng of human Cot 1 DNA (Gibco-BRL) and 2 ug of sonicated salmon sperm DNA in order to suppress possible background produced from repetitive human sequences as well as yeast sequences in the probe. The probes were denatured at 75° C., preannealed at 37° C. for one hour, and applied to denatured chromosome slides prepared from normal male lymphocytes (Korenberg et al., 1995, supra). Post-hybridization washes were performed at 40° C. in 2×SSC/50% formamide followed by washes in 1×SSC at 50° C. Hybridized DNAs were detected with avidin-conjugated fluorescent isothiocyanate (Vector Laboratories). One amplification was performed by using biotinylated anti-avidin. For distinguishing chromosome subbands precisely, a reverse banding technique was used, which was achieved by chromomycin A3 and distamycin A double staining (Korenberg et al., 1995, supra). The color images were captured by using a Photometrics Cooled-CCD camera and BDS image analysis software (Oncor Imaging, Inc.).

PAC and BAC DNA Preparation

Selected clones were grown overnight in LB media containing 12.5 µg/ml kanamycin for PACs and 12.5 µg/ml chloramphenicol for BACs. DNAs were prepared by the alkaline lysis method. PAC DNAs were digested with NotI and subjected to pulsed-field gel electrophoresis. Sizes were determined relative to λ concatamers.

Southern Blot Analysis

Gel electrophoresis of DNA was carried out on 0.8% agarose gels in 1×TBE. Transfer of nucleic acids to Nybond N+ nylon membrane (Amersham) was performed according to the manufacturer's instruction. Probes were labelled using RadPrime Labeling System (BRL). Hybridization was carried out at 42° C. for 16 hours in 50% formamide, 5×SSPE, 5×Denhardt's 0.1% SDS, 100 mg/ml denatured salmon sperm DNA. The filters were washed once in 1×SSC, 0.1% SDS at room temperature for 20 minutes, and twice in 0.1×SSC, 0.1% SDS for 20 minutes at 65° C. The blots were exposed onto X-ray film (Kodak, X-OMAT-AR).

Sequencing of PAC Endclones

PAC clones were inoculated into 500 ml of LB/kanamycin and grown overnight. DNAs were isolated using QIAGEN columns according to the vendors protocol with one additional phenol/chloroform/isoamylalcohol extraction followed by one additional chloroform/isoamylalcohol extraction. Clones were sequenced using the Gibco-BRL cycle sequencing kit with standard T7 and SP6 primers.

Hybridization of $(CAG)_{10}$ Oligonucleotides

Eighty ng of oligonucleotide were 5' end-labeled and hybridized overnight at 42° C. in buffer containing 1 M NaCl, 0.05 M Tris HCl pH7, 5.5 mM EDTA, 0.1% SDS, 1×Denhardt's solution and 200 µg/ml denatured salmon sperm DNA. Filters were washed 2 times with 2×SSC, 0.1% SDS at 55° C. and exposed to Kodak X-ray film for 24 hours, and subsequently washed at 65° C., followed by additional exposure to X-ray film.

Regression Analysis

The data were fit using the Statistical Analysis Software (SAS) package version 3.10 using the Secant Method (Ralston et al, 1978, *Technometrics*, 20:7–14). The regression equation was $y=A*\exp(-ax)$, where y gives the age of onset and x the number of CAG repeats. The conversion criteria were met with the mean square error of 76.598. The value of parameters are as follows: A=1171.583, a=0.091.

EXAMPLE 1

Physical Map of the SCA2 Region

BAC library construction of total human genomic DNA was performed as described in Shizuya et al., *Proc. Natl. Acad. Sci. USA* 89:8794–8797 (1992). BAC clones were screened by PCR using STSs (D12S1228, S29, S32, S33). Insert size of clones was measured by running pulsed-field gel electrophoresis after digesting DNA with NotI.

The marker AFMa128yf1 (D12S1332) which was non-recombinant in several SCA2 pedigrees served as the starting point to assemble a PAC contig. This was done by screening PCR pools of a 3×human PAC library (Ioannou et al., 1994). Two clones were positive for this STS (FIG. 1). Single copy sequences from PAC ends were obtained from P168L1 and used to extend this contig. Subsequent 'walking steps, however, were undertaken by hybridizing PCR-generated STS fragments to gridded membranes of the 3×PAC library and the 1×total human genome BAC library (Research Genetics).

In a similar fashion, a second contig was established starting with the telomeric flanking marker AFM154tc5 (D12S1333). A total of two clones were identified by screening of PCR-pools. After several walking steps, overlap of the two contigs was established by shared STSs (FIG. 1) and by shared restriction fragments (data not shown). All STSs shown in FIG. 1 were mapped back to human chromosome 12 by PCR analysis of a human/Chinese hamster somatic hybrid cell line, HHW582, which contains CHR 12 as the only human chromosome, and by analysis of a chromosome 12 specific lambda library, LL12NS01 (both from Coriell Cell Repositories). Map position in 21q24.1 for clones B295CO5, P191CS and P65I22 was confirmed using FISH (FIG. 1b).

At the same time contigs were constructed for the other flanking markers AFM240wel (D12S1328), AFM291xe9 (D12S1329), and markers WI-4176 and WI-6850 (data not shown). These contigs did not overlap with one another, nor with the AFMa128yf1/AFM154tc5 contig.

All PAC and BAC clones were sized by pulsed-field electrophoresis after digestion with NotI. Overlap of clones was initially determined by shared STS content, and subsequently confirmed by hybridization of selected clones to Southern blots of NotI/XbaI digests of clones.

The dense localization of STSs allowed the precise positioning of YACs that had been identified by screening of PCR pools of the CEPH mega-YAC library with either AFMa128yf1 or AFM154tc5. The only YAC that was positive for both AFMa128yf1 (D12S1332) and AFM154tc5, Y884_h_11, contained an approximately 200 kb interstitial deletion. A small portion of this deletion was not covered by any of the other YAC clones.

EXAMPLE 2

Identification of SCA2-related Trinucleotide Repeats

Since we had observed marked anticipation in one pedigree with SCA2, we identified clones containing trinucleotide repeats. EcoRI digests of a minimal tiling path of PAC clones were hybridized with a $(CAG)_{10}$ nucleotide, as well as other trinucleotide permutations. Three CAG positive bands of distinct sizes were identified in the contig.

PAC clone P65I22 was digested with Sau3A and subcloned into the pBluescript SK(+) phagemid (Stratagene). After transfection into DH5α, bacterial colonies were screened for poly-CAG containing inserts using the methods described above. Positive clones were sequenced using the Circum Vent cycle sequencing kit (New England Biolabs) with end-labeled T3 and T7 primers. However, no reliable sequence could be obtained from the initial plasmid PL65I22. Therefore, this plasmid was digested with BssHII, recloned into the pBluescript plasmid, and CAG-positive clones sequenced with primers corresponding to the following nucleotides of the vector sequence (primer A: 828–848, primer B: 547–565). The sequence of this plasmid, designated PL65I22B, allowed the generation of primers SCA2-A and SCA2-B, which were used to confirm the sequence flanking the CAG repeat.

Plasmid PL65I22B containing an extended CAG repeat that appeared to be embedded into a long open reading frame (ORF) (FIG. 2; SEQ ID NO:1). Sequence analysis of this plasmid appeared to be extremely difficult due to the abundant presence of premature terminations (see below). The CAG repeat in PL65I22B was twice interrupted and had the following structure $(CAG)_8CAA(CAG)_4CAA(CAG)_8$. Four additional PAC clones and one BAC clone contained the SCA2 repeat, and all clones had 22 repeats with two CAA interruptions. Analysis of the genomic DNA sequence flanking the CAG repeat suggested the presence of an open reading frame (see also FIG. 6) and a potential splice site 3' of the CAG repeat (vertical arrow in FIG. 2).

The difficulties encountered in sequencing this region suggested that stable secondary structures might be formed in this GC-rich region. Previous analysis of trinucleotide repeats predisposed to expansion had suggested that these regions are predicted to form hairpin structures. We used an up-dated version of the DNA-FOLD Program (SantaLucia et al., 1996, *Biochemistry*, 35:3555–3562) for secondary structure predictions.

Subsequent analysis of the sequence flanking the CAG repeat using the OLIGO Program indicated that it contained several palindromic sequences predicted to form hairpin loops. Despite the predicted hairpin structures sufficient sequence information was generated to design primers flanking the CAG repeat for the PCR analysis of patient samples.

EXAMPLE 3

Genomic Analysis of an Extended CAG SCA2 Repeat

Using primer pairs SCA2-A and B, genomic DNAs from normal controls and SCA2 patients were amplified and separated by agarose gel electrophoresis. The best results were obtained at an annealing temperature of 63° C. with denaturation times of 90 sec.

Eighty ng each of primers SCA2-A (5'-GGG CCC CTC ACC ATG TCG-3') (SEQ ID NO:6) and SCA2-B (5'-CGG GCT TGC GGA CAT TGG-3') (SEQ ID NO:7) were added to 20 ng of human DNA with standard PCR buffer and nucleotide concentrations. After an initial denaturation at 95° C. for 5 minutes, 35 cycles were repeated with denaturation at 96° C. for 1.5 minutes, an annealing temperature of 63° C. for 30 seconds, extension at 72° C. for 1.5 minutes, and a final extension of 5 minutes at 72° C.

PCR products obtained by PCR amplification of genomic DNAs were separated by electrophoresis through 2% agarose gels in 1×TBE buffer at 10 V/cm. Gels were transferred to nylon membranes (MSI, Westborough, Mass.) using standard procedures for Southern blotting. Membranes were hybridized with a $(CAG)_{10}$ oligonucleotide and processed as described above.

On agarose electrophoresis, a single band of approximately 130 bp was detected in 20 normal individuals, although occasionally two closely spaced bands could be observed. In contrast, all 15 patients with SCA2 from 3 independent families showed one allele in the normal size range and a larger allele ranging from approximately 190 to 250 bp. Southern blot analysis confirmed that both alleles contained CAG repeats.

Figure 3:
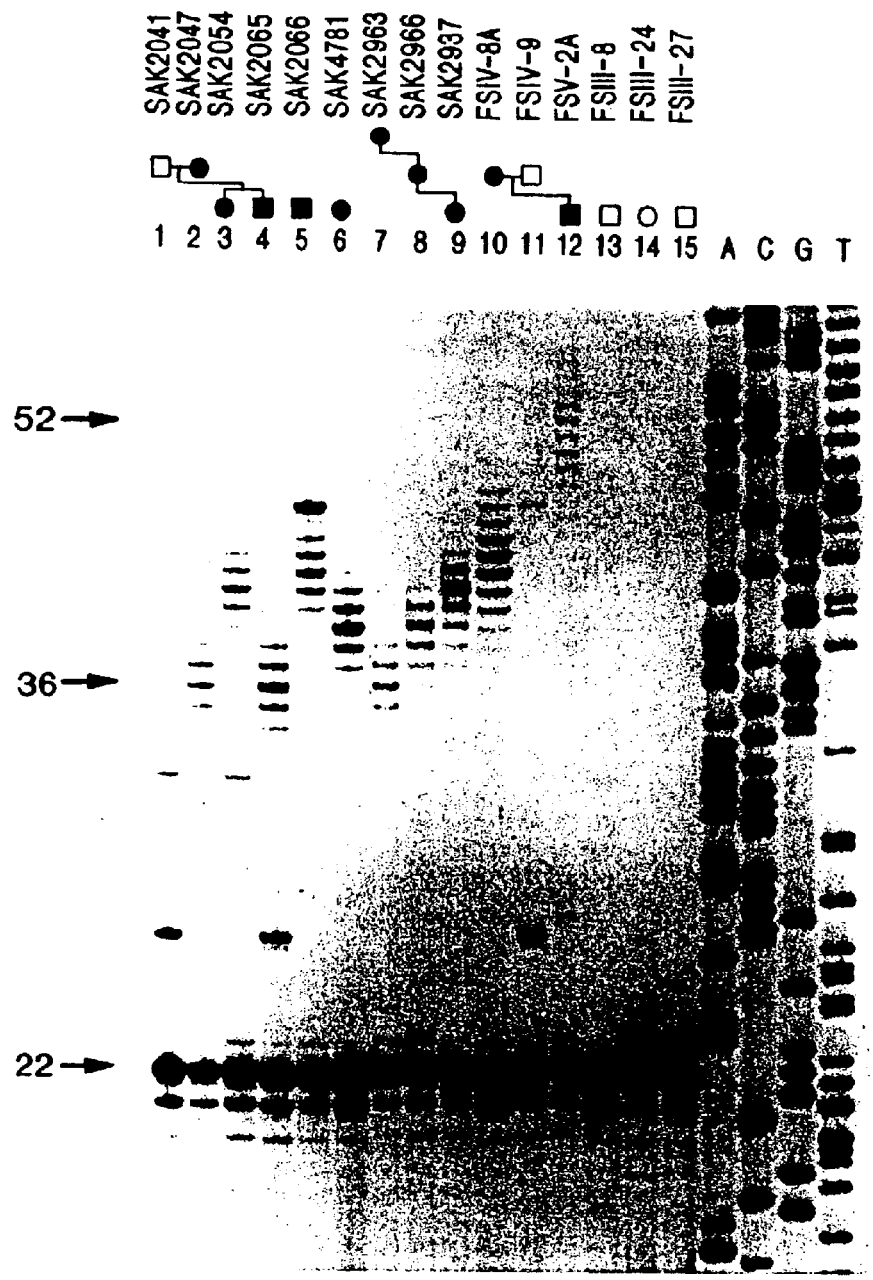
FIG. 3 shows an analysis of the SCA2 CAG repeat by polyacrylamide electrophoresis. A common allele of 22 repeats and a less frequent allele of 23 repeats (samples 14 and 15) are seen in normal individuals. SCA2 patients with extended alleles form 37 to 52 repeats are shown. SCA2 patients derive from two pedigrees with CHR 12 linked dominant ataxia. The pedigree structures are shown at the top. Genomic DNAs were amplified with primers SCA2-A and SCA2-B and separated in a 6% polyacrylamide gel. Primer SCA2-A was end-labeled. As a size standard, single stranded M13mp18 control DNA was sequenced with sequencing primer "-40" provided by USB (United States Biochem.).
Figure 4:
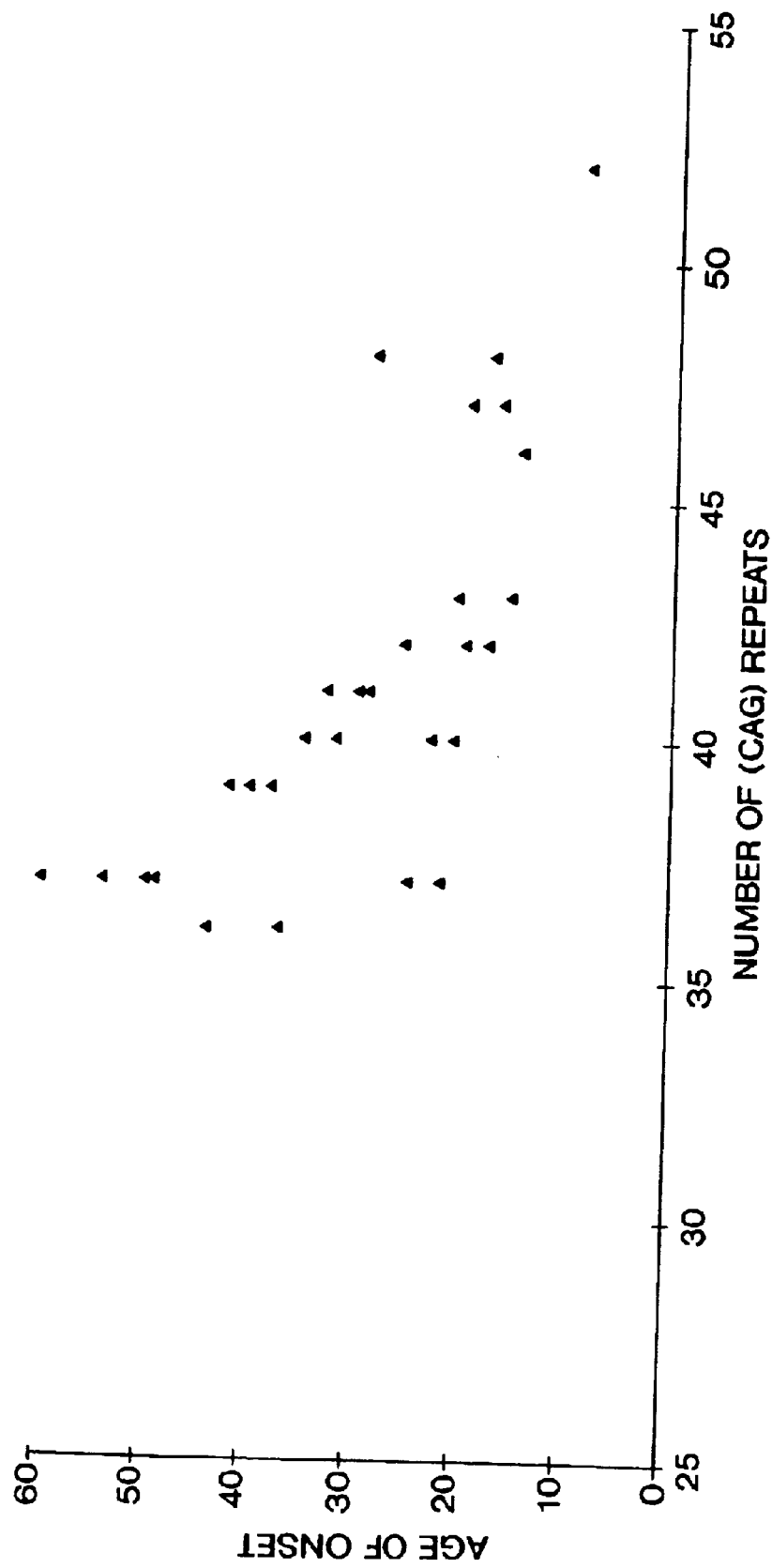
FIG. 4 shows a Scattergram indicating that CAG repeat length and age-of-onset of disease in 33 SCA2 patients are inversely correlated.

To determine the exact sizes of amplified fragments, DNAs from SCA2 patients and 50 normal individuals were amplified and PCR products separated by polyacrylamide gel electrophoresis. A common allele of 22 repeats and a less frequent allele of 23 repeats were observed on normal chromosomes (FIG. 3). The allele frequencies were 0.92 for the smaller and 0.08 for the larger allele. In patients from three independent SCA2 pedigrees, however, extended alleles ranging from 36 to 52 repeats were observed (FIG. 3). Once expanded to the pathologic range, the SCA2 repeat was moderately unstable and further expansion by 2 to 9 repeat units was observed during meiosis (FIG. 3). There was great variability of the age of onset for a given repeat length, especially for disease alleles with 36–40 repeats (FIG. 4). Due to the heterogeneous variance of age of onset we used non-linear regression, and an exponential function was successfully fitted (see methods and FIG. 4). The smallest expansion of 36 repeats was seen in two men with disease onset at ages 37 and 44. The longest expansion of 52 repeats was seen in a boy with disease onset at 9 years of age.

Sequence analysis of ten normal alleles revealed that the common normal allele with 22 repeats contained the two CAA interruptions that were also detected in plasmid PL65I22B. The less frequent normal allele with 23 repeats had lost the 5° CAA interruption, and contained an additional CAG repeat at the 5'-end of the repeat. In three expanded alleles that were isolated from SCA2 patients the CAG repeat lacked any interruptions.

To determine the frequency of mutation in the SCA2 gene in non-Portuguese patients we screened DNAs from 45 independent families with autosomal dominant SCAs. Expansion of the SCA2 repeat was detected in six families. In this set of families, SCA2 expansion was twice as common as expansion in the SCAL gene. In addition to individuals with a 'typical' SCA phenotype, expansion of the SCA2 repeat was detected in a pedigree with a MJD phenotype and one family with SCA and marked dementia.

EXAMPLE 4

Isolation of Human SCA2 cDNA cDNA Library Screen $^{32}$P-labeled probes were generated by PCR amplification of plasmid P65I22B using the following primer pair: 65A3: 5'CCGCGGCTGCCAATGTCC, (SEQ ID NO: 8) 65B5: 5'GTAACCGTTCGGCGCCCG (SEQ ID NO:9). A second probe was generated using primers 65A6: 5'GGCTCCCG-GCGGCTCCTT (SEQ ID NO:10); 65B6: 5'TGCTGCT-GCTGCTGGGGCTTCAG (SEQ ID NO:11). Screening of the trisomy 21 fetal brain cDNA library and the Stratagene adult human frontal cortex cDNA Lamba Zap II library was performed using the amplification products generated from plasmid P65I22B. Phages were plated to an average density of $1 \times 10^5$ per 150 cm$^2$ plate. Plaque lifts of 20 plates ($2 \times 10^6$ phages) were made using duplicated nylon membranes (Duralose-UV, Stratagene). Hybridization and excision were performed according to the manufacturer's protocol. Hybridized membranes were washed to a final stringency of 0.2xSSC, 0.1xSDS at 65 C. The filters were exposed overnight onto X-ray film. Excised phagemids were grown overnight in 5 ml LB medium containing 50 ug/ml of ampicillin.

Figure 5:
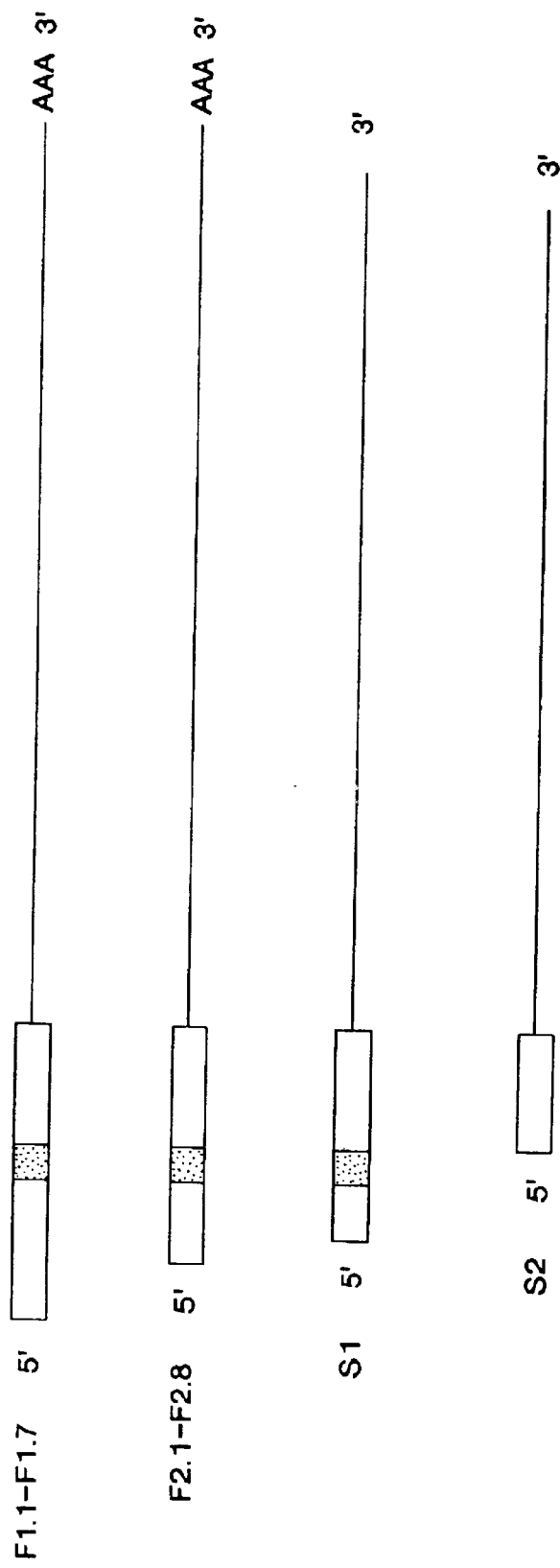
FIG. 5 shows four cDNA clones as a schematic of the composite SCA2 cDNA sequence. The thick line corresponds to coding sequence, the thin line to untranslated regions. The location of the CAG repeat is indicated by a hatched box. In clone S2, the repeat was not a CAG, but a CTG repeat followed by 12 bp of sequence not contained in any of the other cDNA clones.
Figure 8:
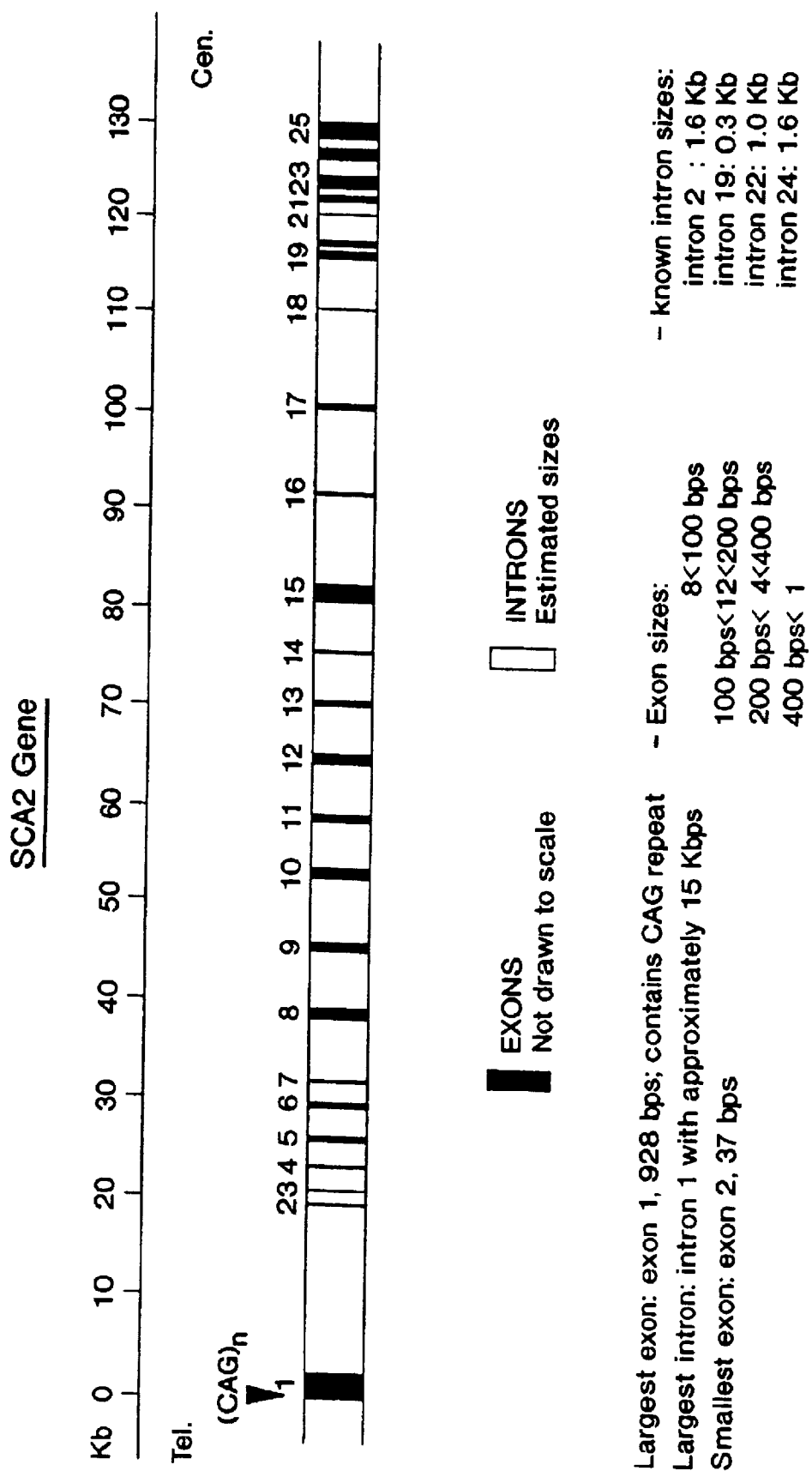
FIG. 8 shows the genomic structure of the SCA2 gene.

Using PCR-generated fragments containing nucleotides 39–237 and 262 to 397 (according to the sequence shown in FIG. 2) we initially screened a human adult frontal cortex library (Stratagene). Through screening of $0.8 \times 10^6$ clones, two positive clones, S1 and S2, were identified. To obtain additional clones, $2 \times 10^6$ clones of a human fetal brain library generated from a fetus with trisomy 21 (Yamakawa et al., 1995, *Hum. Mol. Genet.*, 4:709–716) were screened using the same PCR-generated fragments. A total of 15 clones were obtained, all of which were partially sequenced to determine alignment of clones. These clones appeared to belong to a total of two classes of clones (designated F1.1 through F1.7 and F2.1 through F2.8) that contained long portions of the 3' untranslated region and a poly-A tail (FIG. 5). Both classes of clones extended 40 and 265 bp 5' of the CAG repeat in the coding region of the SCA2 gene.

To obtain cDNA sequence for the 5' end of the SCA2 coding region, placental poly-T selected placental mRNAs (Clontech) were transcribed with MMLV reverse transcriptase and amplified with the following primer pairs: SCA2-A30: 5'CCGCCCGCTCCTCACGTGT (SEQ ID NO:12) SCA2-A31: 5'ACCCCCGAGAAAGCAACC (SEQ ID NO:13); SCA2-B30: 5'-CCGTTGCCGTTGCTACCA (SEQ ID NO:14). The sequences for primers SCA2-A30 and A31 were obtained from genomic sequence, and are located 5' to the stop codon preceding the putative initiator methionine. The sequence for SCA2-B30 was obtained from the 5' end of cDNA clones F1.1 and F1.2. The amplicons obtained by RT-PCR were directly sequenced.

The composite of the human SCA2 cDNA sequence assembled from several overlapping cDNA clones is shown in FIG. 6 (SEQ ID NO:2). The longest open reading frame consists of 3936 bp and ends with a TAA termination codon. The stop codon is followed by 364 bp of 3' untranslated sequence. The CAG repeat is located in the 5'end of the coding region.: The putative translation start site follows an in frame stop codon located 78 bp upstream. The predicted molecular weight for the SCA2 translation product is 140.1 kDa with the CAG trinucleotide repeat predicted to code for glutamine. In analogy to the SCA1 gene product, we propose the name ataxin-2 for the SCA2 gene product.

The cDNA sequence was compared against the GenBank database using the FASTA sequence alignment algorithms and the TIGR database. The predicted protein sequence was compared against the SwissProt database and the predicted translation products of the GenBank database. These searches revealed no significant similarities to genes of known function except for limited homologies to the GLI-Krueppel related protein YY1 (nucleotides 45 to 586, odds against chance occurrence $6.6 \times 10^{-7}$).

However, significant similarities were detected with two partial cDNA transcripts in the TIGR database (THC148678, H03566, odds against chance similarity <10$^{-31}$). Complete sequence analysis of these cDNA clones (purchased from ATCC) revealed significant homologies with ataxin-2. This protein was named ataxin-2 related protein (A2RP). The region showing the most significant homology including a domain of 42 amino acids with 86% identity (codons 243–284 of the consensus sequence) is shown in FIG. 7. This domain is also 100% conserved in mouse ataxin-2. Despite the significant homologies, the polyglutamine tract in ataxin-2 was replaced with an interrupted polyproline tract in the related A2RP human protein and was reduced to one glutamine in the mouse SCA2 homologue (see FIG. 7).

EXAMPLE 6

RT-PCR and Northern Blot Analysis

RNA isolation and reverse transcription was carried out using well-known methods (Huynh et al., 1994, *Hum. Mol. Genet.*,3:1075–1079). RNAs were isolated from lymphoblastoid cell lines established from patients and unrelated spouses in the FS pedigree with SCA2 (Pulst et al., 1993, *Nat. Genet.*, 5:8–10). Multiple tissue Northern blots were purchased from Clontech. For amplification, primers located in two exons (SCA-A and SCA-B14, see also FIG. 6) were chosen so that genomic DNA was not amplified. The sequence for SCA-B14 was: 5'TTCTCATGTGCGGCAT-CAAG (SEQ ID NO15).

Using RT-PCR, it was determined that the SCA2 CAG repeat was transcribed in lymphoblastoid cell lines. In cDNAs from SCA2 patients, transcription from both the normal and the expanded allele was detected using oligonucleotide primers that flank the repeat. By Northern blot analysis, the SCA2 gene was determined to be widely expressed. A strong signal corresponding to a 4.5 kb tran script was detected in all brain regions examined. This transcript was also detected in RNAs isolated from heart, placenta, liver, skeletal muscle, and pancreas. Little transcript was detected in lung and no transcription was detectable in kidney. A much fainter transcript of 7.5 kb could be seen in RNAs isolated from some brain regions and in some peripheral tissues.

EXAMPLE 7

Isolation of Mouse SCA2 cDNA

To identify mouse SCA2 cDNA clones, the Stratagene Lambda ZAP newborn mouse brain cDNA library was screened with a human SCA2 cDNA clone. Six clones were identified and sequenced. A full-length mouse SCA2 cDNA is set forth in SEQ ID NO:4.

SUMMARY OF SEQUENCES

SEQ ID NO:1 is the genomic nucleic acid sequence set forth in FIG. 2.

SEQ ID NO:2 is the nucleic acid sequence (and the deduced amino acid sequence) of a cDNA encoding a human-derived SCA2 protein of the present invention (also set forth in FIG. 6).

SEQ ID NO:3 is the deduced amino acid sequence of the human-derived SCA2 protein set forth in SEQ ID NO:2.

SEQ ID NO:4 is the nucleic acid sequence (and the deduced amino acid sequence) of a cDNA encoding a mouse-derived SCA2 protein of the present invention.

SEQ ID NO:5 is the deduced amino acid sequence of the mouse-derived SCA2 protein set forth in SEQ ID NO:4.

```
                        SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
        (A) LENGTH: 516 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO: 1:

TTGGTAGCAA CGGAAACGGC GGCGGCGCGT TTCGGCCCGG CTCCCGGCGG CTCCTTGGTC      60

TCGGCGGGCC TCCCCGCCCC TTCGTCGTCG TCCTTCTCCC CCTCGCCAGC CCGGGCGCCC     120

CTCCGGCCGC GCCAACCCGC GCCTCCCCGC TCGGCGCCCG TGCGTCCCCG CCGCGTTCCG     180

GCGTCTCCTT GGCGCGCCCG GCTCCCGGCT GTCCCCGCCC GGCGTGCGAG CCGGTGTATG     240

GGCCCCTCAC CATGTCGCTG AAGCCCCAGC AGCAGCAGCA GCAGCAGCAG CAACAGCAGC     300

AGCAGCAACA GCAGCAGCAG CAGCAGCAGC AGCCGCCGCC CGCGGCTGCC AATGTCCGCA     360

AGCCCGGCGG CAGCGGCCTT CTAGCGTCGC CCGCCGCCGC GCCTTCGCCG TCCTCGTCCT     420

CGGTCTCCTC GTCCTCGGCC ACGGCTCCCT CCTCGGTGGT CGCGGCGACC TCCGGCGGCG     480

GGAGGCCCGG CCTGGGCAGG TGGGTGTCGG CACCCC                               516

(2) INFORMATION FOR SEQ ID NO: 2:

(i) SEQUENCE CHARACTERISTICS:
        (A) LENGTH: 4481 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 163..4101

(xi) SEQUENCE DESCRIPTION: SEQ ID NO: 2:

ACCCCCGAGA AAGCAACCCA GCGCGCCGCC CGCTCCTCAC GTGTCCCTCC CGGCCCCGGG       60
```

-continued

```
GCCACCTCAC GTTCTGCTTC CGTCTGACCC CTCCGACTTC CGGTAAAGAG TCCCTATCCG        120

CACCTCCGCT CCCACCCGGC GCCTCGGCGC GCCCGCCCTC CG ATG CGC TCA GCG          174
                                              Met Arg Ser Ala
                                               1

GCC GCA GCT CCT CGG AGT CCC GCG GTG GCC ACC GAG TCT CGC CGC TTC         222
Ala Ala Ala Pro Arg Ser Pro Ala Val Ala Thr Glu Ser Arg Arg Phe
 5              10                  15                  20

GCC GCA GCC AGG TGG CCC GGG TGG CGC TCG CTC CAG CGG CCG GCG CGG         270
Ala Ala Ala Arg Trp Pro Gly Trp Arg Ser Leu Gln Arg Pro Ala Arg
                25                  30                  35

CGG AGC GGG CGG GGC GGC GGT GGC GCG GCC CCG GGA CCG TAT CCC TCC         318
Arg Ser Gly Arg Gly Gly Gly Gly Ala Ala Pro Gly Pro Tyr Pro Ser
            40                  45                  50

GCC GCC CCT CCC CCG CCC GGC CCG GGC CCC CCT CCC TCC CGG CAG AGC         366
Ala Ala Pro Pro Pro Pro Gly Pro Gly Pro Pro Pro Ser Arg Gln Ser
        55                  60                  65

TCG CCT CCC TCC GCC TCA GAC TGT TTT GGT AGC AAC GGC AAC GGC GGC         414
Ser Pro Pro Ser Ala Ser Asp Cys Phe Gly Ser Asn Gly Asn Gly Gly
    70                  75                  80

GGC GCG TTT CGG CCC GGC TCC CGG CGG CTC CTT GGT CTC GGC GGG CCT         462
Gly Ala Phe Arg Pro Gly Ser Arg Arg Leu Leu Gly Leu Gly Gly Pro
85                  90                  95                  100

CCC CGC CCC TTC GTC GTC GTC CTT CTC CCC CTC GCC AGC CCG GGC GCC         510
Pro Arg Pro Phe Val Val Val Leu Leu Pro Leu Ala Ser Pro Gly Ala
                105                 110                 115

CCT CCG GCC GCG CCA ACC CGC GCC TCC CCG CTC GGC GCC CGT GCG TCC         558
Pro Pro Ala Ala Pro Thr Arg Ala Ser Pro Leu Gly Ala Arg Ala Ser
            120                 125                 130

CCG CCG CGT TCC GGC GTC TCC TTG GCG CGC CCG GCT CCC GGC TGT CCC         606
Pro Pro Arg Ser Gly Val Ser Leu Ala Arg Pro Ala Pro Gly Cys Pro
        135                 140                 145

CGC CCG GCG TGC GAG CCG GTG TAT GGG CCC CTC ACC ATG TCG CTG AAG         654
Arg Pro Ala Cys Glu Pro Val Tyr Gly Pro Leu Thr Met Ser Leu Lys
    150                 155                 160

CCC CAG CAG CAG CAG CAG CAG CAG CAA CAG CAG CAG CAG CAA CAG             702
Pro Gln Gln Gln Gln Gln Gln Gln Gln Gln Gln Gln Gln Gln Gln
165                 170                 175                 180

CAG CAG CAG CAG CAG CAG CAG CCG CCG CCC GCG GCT GCC AAT GTC CGC         750
Gln Gln Gln Gln Gln Gln Gln Pro Pro Pro Ala Ala Ala Asn Val Arg
                185                 190                 195

AAG CCC GGC GGC AGC GGC CTT CTA GCG TCG CCC GCC GCC GCG CCT TCG         798
Lys Pro Gly Gly Ser Gly Leu Leu Ala Ser Pro Ala Ala Ala Pro Ser
            200                 205                 210

CCG TCC TCG TCC TCG GTC TCC TCG TCC TCG GCC ACG GCT CCC TCC TCG         846
Pro Ser Ser Ser Ser Val Ser Ser Ser Ser Ala Thr Ala Pro Ser Ser
        215                 220                 225

GTG GTC GCG GCG ACC TCC GGC GGC GGG AGG CCC GGC CTG GGC AGA GGT         894
Val Val Ala Ala Thr Ser Gly Gly Gly Arg Pro Gly Leu Gly Arg Gly
    230                 235                 240

CGA AAC AGT AAC AAA GGA CTG CCT CAG TCT ACG ATT TCT TTT GAT GGA         942
Arg Asn Ser Asn Lys Gly Leu Pro Gln Ser Thr Ile Ser Phe Asp Gly
245                 250                 255                 260

ATC TAT GCA AAT ATG AGG ATG GTT CAT ATA CTT ACA TCA GTT GTT GGC         990
Ile Tyr Ala Asn Met Arg Met Val His Ile Leu Thr Ser Val Val Gly
                265                 270                 275

TCC AAA TGT GAA GTA CAA GTG AAA AAT GGA GGT ATA TAT GAA GGA GTT        1038
Ser Lys Cys Glu Val Gln Val Lys Asn Gly Gly Ile Tyr Glu Gly Val
            280                 285                 290

TTT AAA ACT TAC AGT CCG AAG TGT GAT TTG GTA CTT GAT GCC GCA CAT        1086
```

-continued

```
             Phe Lys Thr Tyr Ser Pro Lys Cys Asp Leu Val Leu Asp Ala Ala His
                     295                 300                 305

GAG AAA AGT ACA GAA TCC AGT TCG GGG CCG AAA CGT GAA GAA ATA ATG        1134
Glu Lys Ser Thr Glu Ser Ser Ser Gly Pro Lys Arg Glu Glu Ile Met
        310                 315                 320

GAG AGT ATT TTG TTC AAA TGT TCA GAC TTT GTT GTG GTA CAG TTT AAA        1182
Glu Ser Ile Leu Phe Lys Cys Ser Asp Phe Val Val Val Gln Phe Lys
325                 330                 335                 340

GAT ATG GAC TCC AGT TAT GCA AAA AGA GAT GCT TTT ACT GAC TCT GCT        1230
Asp Met Asp Ser Ser Tyr Ala Lys Arg Asp Ala Phe Thr Asp Ser Ala
                345                 350                 355

ATC AGT GCT AAA GTG AAT GGC GAA CAC AAA GAG AAG GAC CTG GAG CCC        1278
Ile Ser Ala Lys Val Asn Gly Glu His Lys Glu Lys Asp Leu Glu Pro
        360                 365                 370

TGG GAT GCA GGT GAA CTC ACA GCC AAT GAG GAA CTT GAG GCT TTG GAA        1326
Trp Asp Ala Gly Glu Leu Thr Ala Asn Glu Glu Leu Glu Ala Leu Glu
                375                 380                 385

AAT GAC GTA TCT AAT GGA TGG GAT CCC AAT GAT ATG TTT CGA TAT AAT        1374
Asn Asp Val Ser Asn Gly Trp Asp Pro Asn Asp Met Phe Arg Tyr Asn
        390                 395                 400

GAA GAA AAT TAT GGT GTA GTG TCT ACG TAT GAT AGC AGT TTA TCT TCG        1422
Glu Glu Asn Tyr Gly Val Val Ser Thr Tyr Asp Ser Ser Leu Ser Ser
405                 410                 415                 420

TAT ACA GTG CCC TTA GAA AGA GAT AAC TCA GAA GAA TTT TTA AAA CGG        1470
Tyr Thr Val Pro Leu Glu Arg Asp Asn Ser Glu Glu Phe Leu Lys Arg
                425                 430                 435

GAA GCA AGG GCA AAC CAG TTA GCA GAA GAA ATT GAG TCA AGT GCC CAG        1518
Glu Ala Arg Ala Asn Gln Leu Ala Glu Glu Ile Glu Ser Ser Ala Gln
        440                 445                 450

TAC AAA GCT CGA GTG GCC CTG GAA AAT GAT GAT AGG AGT GAG GAA GAA        1566
Tyr Lys Ala Arg Val Ala Leu Glu Asn Asp Asp Arg Ser Glu Glu Glu
                455                 460                 465

AAA TAC ACA GCA GTT CAG AGA AAT TCC AGT GAA CGT GAG GGG CAC AGC        1614
Lys Tyr Thr Ala Val Gln Arg Asn Ser Ser Glu Arg Glu Gly His Ser
        470                 475                 480

ATA AAC ACT AGG GAA AAT AAA TAT ATT CCT CCT GGA CAA AGA AAT AGA        1662
Ile Asn Thr Arg Glu Asn Lys Tyr Ile Pro Pro Gly Gln Arg Asn Arg
485                 490                 495                 500

GAA GTC ATA TCC TGG GGA AGT GGG AGA CAG AAT TCA CCG CGT ATG GGC        1710
Glu Val Ile Ser Trp Gly Ser Gly Arg Gln Asn Ser Pro Arg Met Gly
                505                 510                 515

CAG CCT GGA TCG GGC TCC ATG CCA TCA AGA TCC ACT TCT CAC ACT TCA        1758
Gln Pro Gly Ser Gly Ser Met Pro Ser Arg Ser Thr Ser His Thr Ser
        520                 525                 530

GAT TTC AAC CCG AAT TCT GGT TCA GAC CAA AGA GTA GTT AAT GGA GGT        1806
Asp Phe Asn Pro Asn Ser Gly Ser Asp Gln Arg Val Val Asn Gly Gly
                535                 540                 545

GTT CCC TGG CCA TCG CCT TGC CCA TCT CCT TCC TCT CGC CCA CCT TCT        1854
Val Pro Trp Pro Ser Pro Cys Pro Ser Pro Ser Ser Arg Pro Pro Ser
        550                 555                 560

CGC TAC CAG TCA GGT CCC AAC TCT CTT CCA CCT CGG GCA GCC ACC CCT        1902
Arg Tyr Gln Ser Gly Pro Asn Ser Leu Pro Pro Arg Ala Ala Thr Pro
565                 570                 575                 580

ACA CGG CCG CCC TCC AGG CCC CCC TCG CGG CCA TCC AGA CCC CCG TCT        1950
Thr Arg Pro Pro Ser Arg Pro Pro Ser Arg Pro Ser Arg Pro Pro Ser
                585                 590                 595

CAC CCC TCT GCT CAT GGT TCT CCA GCT CCT GTC TCT ACT ATG CCT AAA        1998
His Pro Ser Ala His Gly Ser Pro Ala Pro Val Ser Thr Met Pro Lys
        600                 605                 610
```

```
                                                          -continued

CGC ATG TCT TCA GAA GGG CCT CCA AGG ATG TCC CCA AAG GCC CAG CGA        2046
Arg Met Ser Ser Glu Gly Pro Pro Arg Met Ser Pro Lys Ala Gln Arg
        615                 620                 625

CAT CCT CGA AAT CAC AGA GTT TCT GCT GGG AGG GGT TCC ATA TCC AGT        2094
His Pro Arg Asn His Arg Val Ser Ala Gly Arg Gly Ser Ile Ser Ser
630                 635                 640

GGC CTA GAA TTT GTA TCC CAC AAC CCA CCC AGT GAA GCA GCT ACT CCT        2142
Gly Leu Glu Phe Val Ser His Asn Pro Pro Ser Glu Ala Ala Thr Pro
645                 650                 655                 660

CCA GTA GCA AGG ACC AGT CCC TCG GGG GGA ACG TGG TCA TCA GTG GTC        2190
Pro Val Ala Arg Thr Ser Pro Ser Gly Gly Thr Trp Ser Ser Val Val
                665                 670                 675

AGT GGG GTT CCA AGA TTA TCC CCT AAA ACT CAT AGA CCC AGG TCT CCC        2238
Ser Gly Val Pro Arg Leu Ser Pro Lys Thr His Arg Pro Arg Ser Pro
            680                 685                 690

AGA CAG AAC AGT ATT GGA AAT ACC CCC AGT GGG CCA GTT CTT GCT TCT        2286
Arg Gln Asn Ser Ile Gly Asn Thr Pro Ser Gly Pro Val Leu Ala Ser
        695                 700                 705

CCC CAA GCT GGT ATT ATT CCA ACT GAA GCT GTT GCC ATG CCT ATT CCA        2334
Pro Gln Ala Gly Ile Ile Pro Thr Glu Ala Val Ala Met Pro Ile Pro
    710                 715                 720

GCT GCA TCT CCT ACG CCT GCT AGT CCT GCA TCG AAC AGA GCT GTT ACC        2382
Ala Ala Ser Pro Thr Pro Ala Ser Pro Ala Ser Asn Arg Ala Val Thr
725                 730                 735                 740

CCT TCT AGT GAG GCT AAA GAT TCC AGG CTT CAA GAT CAG AGG CAG AAC        2430
Pro Ser Ser Glu Ala Lys Asp Ser Arg Leu Gln Asp Gln Arg Gln Asn
                745                 750                 755

TCT CCT GCA GGG AAT AAA GAA AAT ATT AAA CCC AAT GAA ACA TCA CCT        2478
Ser Pro Ala Gly Asn Lys Glu Asn Ile Lys Pro Asn Glu Thr Ser Pro
            760                 765                 770

AGC TTC TCA AAA GCT GAA AAC AAA GGT ATA TCA CCA GTT GTT TCT GAA        2526
Ser Phe Ser Lys Ala Glu Asn Lys Gly Ile Ser Pro Val Val Ser Glu
        775                 780                 785

CAT AGA AAA CAG ATT GAT GAT TTA AAG AAA TTT AAG AAT GAT TTT AGG        2574
His Arg Lys Gln Ile Asp Asp Leu Lys Lys Phe Lys Asn Asp Phe Arg
    790                 795                 800

TTA CAG CCA AGT TCT ACT TCT GAA TCT ATG GAT CAA CTA CTA AAC AAA        2622
Leu Gln Pro Ser Ser Thr Ser Glu Ser Met Asp Gln Leu Leu Asn Lys
805                 810                 815                 820

AAT AGA GAG GGA GAA AAA TCA AGA GAT TTG ATC AAA GAC AAA ATT GAA        2670
Asn Arg Glu Gly Glu Lys Ser Arg Asp Leu Ile Lys Asp Lys Ile Glu
                825                 830                 835

CCA AGT GCT AAG GAT TCT TTC ATT GAA AAT AGC AGC AGC AAC TGT ACC        2718
Pro Ser Ala Lys Asp Ser Phe Ile Glu Asn Ser Ser Ser Asn Cys Thr
            840                 845                 850

AGT GGC AGC AGC AAG CCG AAT AGC CCC AGC ATT TCC CCT TCA ATA CTT        2766
Ser Gly Ser Ser Lys Pro Asn Ser Pro Ser Ile Ser Pro Ser Ile Leu
        855                 860                 865

AGT AAC ACG GAG CAC AAG AGG GGA CCT GAG GTC ACT TCC CAA GGG GTT        2814
Ser Asn Thr Glu His Lys Arg Gly Pro Glu Val Thr Ser Gln Gly Val
    870                 875                 880

CAG ACT TCC AGC CCA GCA TGT AAA CAA GAG AAA GAC GAT AAG GAA GAG        2862
Gln Thr Ser Ser Pro Ala Cys Lys Gln Glu Lys Asp Asp Lys Glu Glu
885                 890                 895                 900

AAG AAA GAC GCA GCT GAG CAA GTT AGG AAA TCA ACA TTG AAT CCC AAT        2910
Lys Lys Asp Ala Ala Glu Gln Val Arg Lys Ser Thr Leu Asn Pro Asn
                905                 910                 915

GCA AAG GAG TTC AAC CCA CGT TCC TTC TCT CAG CCA AAG CCT TCT ACT        2958
Ala Lys Glu Phe Asn Pro Arg Ser Phe Ser Gln Pro Lys Pro Ser Thr
            920                 925                 930
```

| | |
|---|---|
| ACC CCA ACT TCA CCT CGG CCT CAA GCA CAA CCT AGC CCA TCT ATG GTG<br>Thr Pro Thr Ser Pro Arg Pro Gln Ala Gln Pro Ser Pro Ser Met Val<br>          935                       940                  945 | 3006 |
| GGT CAT CAA CAG CCA ACT CCA GTT TAT ACT CAG CCT GTT TGT TTT GCA<br>Gly His Gln Gln Pro Thr Pro Val Tyr Thr Gln Pro Val Cys Phe Ala<br>       950                     955                   960 | 3054 |
| CCA AAT ATG ATG TAT CCA GTC CCA GTG AGC CCA GGC GTG CAA CCT TTA<br>Pro Asn Met Met Tyr Pro Val Pro Val Ser Pro Gly Val Gln Pro Leu<br>965                   970                   975                 980 | 3102 |
| TAC CCA ATA CCT ATG ACG CCC ATG CCA GTG AAT CAA GCC AAG ACA TAT<br>Tyr Pro Ile Pro Met Thr Pro Met Pro Val Asn Gln Ala Lys Thr Tyr<br>                    985                     990                 995 | 3150 |
| AGA GCA GTA CCA AAT ATG CCC CAA CAG CGG CAA GAC CAG CAT CAT CAG<br>Arg Ala Val Pro Asn Met Pro Gln Gln Arg Gln Asp Gln His His Gln<br>              1000                   1005                1010 | 3198 |
| AGT GCC ATG ATG CAC CCA GCG TCA GCA GCG GGC CCA CCG ATT GCA GCC<br>Ser Ala Met Met His Pro Ala Ser Ala Ala Gly Pro Pro Ile Ala Ala<br>           1015                   1020                 1025 | 3246 |
| ACC CCA CCA GCT TAC TCC ACG CAA TAT GTT GCC TAC AGT CCT CAG CAG<br>Thr Pro Pro Ala Tyr Ser Thr Gln Tyr Val Ala Tyr Ser Pro Gln Gln<br>          1030                   1035                1040 | 3294 |
| TTC CCA AAT CAG CCC CTT GTT CAG CAT GTG CCA CAT TAT CAG TCT CAG<br>Phe Pro Asn Gln Pro Leu Val Gln His Val Pro His Tyr Gln Ser Gln<br>1045                 1050                 1055               1060 | 3342 |
| CAT CCT CAT GTC TAT AGT CCT GTA ATA CAG GGT AAT GCT AGA ATG ATG<br>His Pro His Val Tyr Ser Pro Val Ile Gln Gly Asn Ala Arg Met Met<br>                   1065                1070                1075 | 3390 |
| GCA CCA CCA ACA CAC GCC CAG CCT GGT TTA GTA TCT TCT TCA GCA ACT<br>Ala Pro Pro Thr His Ala Gln Pro Gly Leu Val Ser Ser Ser Ala Thr<br>           1080                   1085                1090 | 3438 |
| CAG TAC GGG GCT CAT GAG CAG ACG CAT GCG ATG TAT GCA TGT CCC AAA<br>Gln Tyr Gly Ala His Glu Gln Thr His Ala Met Tyr Ala Cys Pro Lys<br>          1095                   1100                1105 | 3486 |
| TTA CCA TAC AAC AAG GAG ACA AGC CCT TCT TTC TAC TTT GCC ATT TCC<br>Leu Pro Tyr Asn Lys Glu Thr Ser Pro Ser Phe Tyr Phe Ala Ile Ser<br>          1110                   1115                1120 | 3534 |
| ACG GGC TCC CTT GCT CAG CAG TAT GCG CAC CCT AAC GCT ACC CTG CAC<br>Thr Gly Ser Leu Ala Gln Gln Tyr Ala His Pro Asn Ala Thr Leu His<br>1125                 1130                 1135               1140 | 3582 |
| CCA CAT ACT CCA CAC CCT CAG CCT TCA GCT ACC CCC ACT GGA CAG CAG<br>Pro His Thr Pro His Pro Gln Pro Ser Ala Thr Pro Thr Gly Gln Gln<br>                   1145                1150                1155 | 3630 |
| CAA AGC CAA CAT GGT GGA AGT CAT CCT GCA CCC AGT CCT GTT CAG CAC<br>Gln Ser Gln His Gly Gly Ser His Pro Ala Pro Ser Pro Val Gln His<br>              1160                   1165                1170 | 3678 |
| CAT CAG CAC CAG GCC GCC CAG GCT CTC CAT CTG GCC AGT CCA CAG CAG<br>His Gln His Gln Ala Ala Gln Ala Leu His Leu Ala Ser Pro Gln Gln<br>          1175                   1180                1185 | 3726 |
| CAG TCA GCC ATT TAC CAC GCG GGG CTT GCG CCA ACT CCA CCC TCC ATG<br>Gln Ser Ala Ile Tyr His Ala Gly Leu Ala Pro Thr Pro Pro Ser Met<br>          1190                   1195                1200 | 3774 |
| ACA CCT GCC TCC AAC ACG CAG TCG CCA CAG AAT AGT TTC CCA GCA GCA<br>Thr Pro Ala Ser Asn Thr Gln Ser Pro Gln Asn Ser Phe Pro Ala Ala<br>1205                 1210                 1215               1220 | 3822 |
| CAA CAG ACT GTC TTT ACG ATC CAT CCT TCT CAC GTT CAG CCG GCG TAT<br>Gln Gln Thr Val Phe Thr Ile His Pro Ser His Val Gln Pro Ala Tyr<br>                   1225                1230                1235 | 3870 |
| ACC AAC CCA CCC CAC ATG GCC CAC GTA CCT CAG GCT CAT GTA CAG TCA<br>Thr Asn Pro Pro His Met Ala His Val Pro Gln Ala His Val Gln Ser | 3918 |

-continued

```
                1240              1245              1250
GGA ATG GTT CCT TCT CAT CCA ACT GCC CAT GCG CCA ATG ATG CTA ATG         3966
Gly Met Val Pro Ser His Pro Thr Ala His Ala Pro Met Met Leu Met
        1255              1260              1265

ACG ACA CAG CCA CCC GGC GGT CCC CAG GCC GCC CTC GCT CAA AGT GCA         4014
Thr Thr Gln Pro Pro Gly Gly Pro Gln Ala Ala Leu Ala Gln Ser Ala
        1270              1275              1280

CTA CAG CCC ATT CCA GTC TCG ACA ACA GCG CAT TTC CCC TAT ATG ACG         4062
Leu Gln Pro Ile Pro Val Ser Thr Thr Ala His Phe Pro Tyr Met Thr
1285              1290              1295              1300

CAC CCT TCA GTA CAA GCC CAC CAC CAA CAG CAG TTG TAA GGCTGCCCTG          4111
His Pro Ser Val Gln Ala His His Gln Gln Gln Leu  *
                1305              1310

GAGGAACCGA AAGGCAAAT TCCCTCCTCC CTTCTACTGC TTCTACCAAC TGGAAGCACA         4171

GAAAACTAGA ATTTCATTTA TTTTGTTTTT AAAATATATA TGTTGATTTC TTGTAACATC         4231

CAATAGGAAT GCTAACAGTT CACTTGCAGT GGAAGATACT TGGACCGAGT AGAGGCATTT         4291

AGGAACTTGG GGGCTATTCC ATAATTCCAT ATGCTGTTTC AGAGTCCCGC AGGTACCCCA         4351

GCTCTGCTTG CCGAAACTGG AAGTTATTTA TTTTTTAATA ACCCTTGAAA GTCATGAACA         4411

CATCAGCTAG CAAAAGAAGT AACAAGAGTG ATTCTTGCTG CTATTACTGC TAAAAAAAAA         4471

AAAAAAAAA                                                                 4481
```

(2) INFORMATION FOR SEQ ID NO: 3:

(i) SEQUENCE CHARACTERISTICS:
      (A) LENGTH: 1312 amino acids
      (B) TYPE: amino acid
      (D) TOPOLOGY: linear (ii) MOLECULE TYPE: protein (xi) SEQUENCE DESCRIPTION: SEQ ID NO: 3:

```
Met Arg Ser Ala Ala Ala Ala Pro Arg Ser Pro Ala Val Ala Thr Glu
 1               5                  10                  15

Ser Arg Arg Phe Ala Ala Ala Arg Trp Pro Gly Trp Arg Ser Leu Gln
            20                  25                  30

Arg Pro Ala Arg Arg Ser Gly Arg Gly Gly Gly Ala Ala Pro Gly
        35                  40                  45

Pro Tyr Pro Ser Ala Ala Pro Pro Pro Gly Pro Gly Pro Pro Pro
    50                  55                  60

Ser Arg Gln Ser Ser Pro Pro Ser Ala Ser Asp Cys Phe Gly Ser Asn
65                  70                  75                  80

Gly Asn Gly Gly Gly Ala Phe Arg Pro Gly Ser Arg Arg Leu Leu Gly
                85                  90                  95

Leu Gly Gly Pro Pro Arg Pro Phe Val Val Leu Pro Leu Ala
            100                 105                 110

Ser Pro Gly Ala Pro Pro Ala Ala Pro Thr Arg Ala Ser Pro Leu Gly
            115                 120                 125

Ala Arg Ala Ser Pro Pro Arg Ser Gly Val Ser Leu Ala Arg Pro Ala
130                 135                 140

Pro Gly Cys Pro Arg Pro Ala Cys Glu Pro Val Tyr Gly Pro Leu Thr
145                 150                 155                 160

Met Ser Leu Lys Pro Gln Gln Gln Gln Gln Gln Gln Gln Gln
                165                 170                 175

Gln Gln Gln Gln Gln Gln Gln Gln Gln Gln Pro Pro Pro Ala Ala
            180                 185                 190
```

```
Ala Asn Val Arg Lys Pro Gly Gly Ser Gly Leu Leu Ala Ser Pro Ala
        195                 200                 205

Ala Ala Pro Ser Pro Ser Ser Ser Val Ser Ser Ser Ala Thr
210                 215                 220

Ala Pro Ser Ser Val Val Ala Ala Thr Ser Gly Gly Gly Arg Pro Gly
225                 230                 235                 240

Leu Gly Arg Gly Arg Asn Ser Asn Lys Gly Leu Pro Gln Ser Thr Ile
            245                 250                 255

Ser Phe Asp Gly Ile Tyr Ala Asn Met Arg Met Val His Ile Leu Thr
            260                 265                 270

Ser Val Val Gly Ser Lys Cys Glu Val Gln Val Lys Asn Gly Gly Ile
        275                 280                 285

Tyr Glu Gly Val Phe Lys Thr Tyr Ser Pro Lys Cys Asp Leu Val Leu
        290                 295                 300

Asp Ala Ala His Glu Lys Ser Thr Glu Ser Ser Ser Gly Pro Lys Arg
305                 310                 315                 320

Glu Glu Ile Met Glu Ser Ile Leu Phe Lys Cys Ser Asp Phe Val Val
            325                 330                 335

Val Gln Phe Lys Asp Met Asp Ser Ser Tyr Ala Lys Arg Asp Ala Phe
            340                 345                 350

Thr Asp Ser Ala Ile Ser Ala Lys Val Asn Gly Glu His Lys Glu Lys
            355                 360                 365

Asp Leu Glu Pro Trp Asp Ala Gly Glu Leu Thr Ala Asn Glu Glu Leu
        370                 375                 380

Glu Ala Leu Glu Asn Asp Val Ser Asn Gly Trp Asp Pro Asn Asp Met
385                 390                 395                 400

Phe Arg Tyr Asn Glu Glu Asn Tyr Gly Val Val Ser Thr Tyr Asp Ser
            405                 410                 415

Ser Leu Ser Ser Tyr Thr Val Pro Leu Glu Arg Asp Asn Ser Glu Glu
            420                 425                 430

Phe Leu Lys Arg Glu Ala Arg Ala Asn Gln Leu Ala Glu Glu Ile Glu
        435                 440                 445

Ser Ser Ala Gln Tyr Lys Ala Arg Val Ala Leu Glu Asn Asp Asp Arg
450                 455                 460

Ser Glu Glu Glu Lys Tyr Thr Ala Val Gln Arg Asn Ser Ser Glu Arg
465                 470                 475                 480

Glu Gly His Ser Ile Asn Thr Arg Glu Asn Lys Tyr Ile Pro Pro Gly
            485                 490                 495

Gln Arg Asn Arg Glu Val Ile Ser Trp Gly Ser Gly Arg Gln Asn Ser
            500                 505                 510

Pro Arg Met Gly Gln Pro Gly Ser Gly Ser Met Pro Ser Arg Ser Thr
        515                 520                 525

Ser His Thr Ser Asp Phe Asn Pro Asn Ser Gly Ser Asp Gln Arg Val
        530                 535                 540

Val Asn Gly Gly Val Pro Trp Pro Ser Pro Cys Pro Ser Pro Ser Ser
545                 550                 555                 560

Arg Pro Pro Ser Arg Tyr Gln Ser Gly Pro Asn Ser Leu Pro Pro Arg
            565                 570                 575

Ala Ala Thr Pro Thr Arg Pro Pro Ser Arg Pro Ser Arg Pro Ser
        580                 585                 590

Arg Pro Pro Ser His Pro Ser Ala His Gly Ser Pro Ala Pro Val Ser
        595                 600                 605
```

```
Thr Met Pro Lys Arg Met Ser Ser Glu Gly Pro Pro Arg Met Ser Pro
    610                 615                 620
Lys Ala Gln Arg His Pro Arg Asn His Arg Val Ser Ala Gly Arg Gly
625                 630                 635                 640
Ser Ile Ser Ser Gly Leu Glu Phe Val Ser His Asn Pro Pro Ser Glu
                645                 650                 655
Ala Ala Thr Pro Pro Val Ala Arg Thr Ser Pro Ser Gly Gly Thr Trp
            660                 665                 670
Ser Ser Val Val Ser Gly Val Pro Arg Leu Ser Pro Lys Thr His Arg
        675                 680                 685
Pro Arg Ser Pro Arg Gln Asn Ser Ile Gly Asn Thr Pro Ser Gly Pro
690                 695                 700
Val Leu Ala Ser Pro Gln Ala Gly Ile Ile Pro Thr Glu Ala Val Ala
705                 710                 715                 720
Met Pro Ile Pro Ala Ala Ser Pro Thr Pro Ala Ser Pro Ala Ser Asn
                725                 730                 735
Arg Ala Val Thr Pro Ser Ser Glu Ala Lys Asp Ser Arg Leu Gln Asp
            740                 745                 750
Gln Arg Gln Asn Ser Pro Ala Gly Asn Lys Glu Asn Ile Lys Pro Asn
        755                 760                 765
Glu Thr Ser Pro Ser Phe Ser Lys Ala Glu Asn Lys Gly Ile Ser Pro
770                 775                 780
Val Val Ser Glu His Arg Lys Gln Ile Asp Asp Leu Lys Lys Phe Lys
785                 790                 795                 800
Asn Asp Phe Arg Leu Gln Pro Ser Ser Thr Ser Glu Ser Met Asp Gln
                805                 810                 815
Leu Leu Asn Lys Asn Arg Glu Gly Glu Lys Ser Arg Asp Leu Ile Lys
            820                 825                 830
Asp Lys Ile Glu Pro Ser Ala Lys Asp Ser Phe Ile Glu Asn Ser Ser
        835                 840                 845
Ser Asn Cys Thr Ser Gly Ser Ser Lys Pro Asn Ser Pro Ser Ile Ser
850                 855                 860
Pro Ser Ile Leu Ser Asn Thr Glu His Lys Arg Gly Pro Glu Val Thr
865                 870                 875                 880
Ser Gln Gly Val Gln Thr Ser Ser Pro Ala Cys Lys Gln Glu Lys Asp
                885                 890                 895
Asp Lys Glu Glu Lys Lys Asp Ala Ala Glu Gln Val Arg Lys Ser Thr
            900                 905                 910
Leu Asn Pro Asn Ala Lys Glu Phe Asn Pro Arg Ser Phe Ser Gln Pro
        915                 920                 925
Lys Pro Ser Thr Thr Pro Thr Ser Pro Arg Pro Gln Ala Gln Pro Ser
930                 935                 940
Pro Ser Met Val Gly His Gln Gln Pro Thr Pro Val Tyr Thr Gln Pro
945                 950                 955                 960
Val Cys Phe Ala Pro Asn Met Met Tyr Pro Val Pro Val Ser Pro Gly
                965                 970                 975
Val Gln Pro Leu Tyr Pro Ile Pro Met Thr Pro Met Pro Val Asn Gln
            980                 985                 990
Ala Lys Thr Tyr Arg Ala Val Pro Asn Met Pro Gln Gln Arg Gln Asp
        995                 1000                1005
Gln His His Gln Ser Ala Met Met His Pro Ala Ser Ala Ala Gly Pro
1010                1015                1020
Pro Ile Ala Ala Thr Pro Pro Ala Tyr Ser Thr Gln Tyr Val Ala Tyr
```

```
                    1025                1030                1035                1040
            Ser Pro Gln Gln Phe Pro Asn Gln Pro Leu Val Gln His Val Pro His
                        1045                1050                1055
            Tyr Gln Ser Gln His Pro His Val Tyr Ser Pro Val Ile Gln Gly Asn
                        1060                1065                1070
            Ala Arg Met Met Ala Pro Pro Thr His Ala Gln Pro Gly Leu Val Ser
                        1075                1080                1085
            Ser Ser Ala Thr Gln Tyr Gly Ala His Glu Gln Thr His Ala Met Tyr
                        1090                1095                1100
            Ala Cys Pro Lys Leu Pro Tyr Asn Lys Glu Thr Ser Pro Ser Phe Tyr
            1105                1110                1115                1120
            Phe Ala Ile Ser Thr Gly Ser Leu Ala Gln Gln Tyr Ala His Pro Asn
                        1125                1130                1135
            Ala Thr Leu His Pro His Thr Pro His Pro Gln Pro Ser Ala Thr Pro
                        1140                1145                1150
            Thr Gly Gln Gln Gln Ser Gln His Gly Gly Ser His Pro Ala Pro Ser
                        1155                1160                1165
            Pro Val Gln His His Gln His Gln Ala Ala Gln Ala Leu His Leu Ala
                        1170                1175                1180
            Ser Pro Gln Gln Gln Ser Ala Ile Tyr His Ala Gly Leu Ala Pro Thr
            1185                1190                1195                1200
            Pro Pro Ser Met Thr Pro Ala Ser Asn Thr Gln Ser Pro Gln Asn Ser
                        1205                1210                1215
            Phe Pro Ala Ala Gln Gln Thr Val Phe Thr Ile His Pro Ser His Val
                        1220                1225                1230
            Gln Pro Ala Tyr Thr Asn Pro Pro His Met Ala His Val Pro Gln Ala
                        1235                1240                1245
            His Val Gln Ser Gly Met Val Pro Ser His Pro Thr Ala His Ala Pro
                        1250                1255                1260
            Met Met Leu Met Thr Thr Gln Pro Pro Gly Gly Pro Gln Ala Ala Leu
            1265                1270                1275                1280
            Ala Gln Ser Ala Leu Gln Pro Ile Pro Val Ser Thr Thr Ala His Phe
                        1285                1290                1295
            Pro Tyr Met Thr His Pro Ser Val Gln Ala His His Gln Gln Gln Leu
                        1300                1305                1310

(2) INFORMATION FOR SEQ ID NO: 4:

(i) SEQUENCE CHARACTERISTICS:
        (A) LENGTH: 3798 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 50..3457

(xi) SEQUENCE DESCRIPTION: SEQ ID NO: 4:

GGCACGAGGT CCCCGCCCGG CGTGCGAGCC GGTGTATGGG CCGCTCACC ATG TCG        55
                                                      Met Ser
                                                       1

CTG AAG CCG CAG CCG CAG CCG CCC GCG CCC GCC ACT GGC CGC AAG CCC    103
Leu Lys Pro Gln Pro Gln Pro Pro Ala Pro Ala Thr Gly Arg Lys Pro
       5                  10                  15

GGC GGC GGC CTG CTC TCG TCG CCC GGC GCC GCG CCG GCC TCG GCC GCG    151
```

```
                -continued

Gly Gly Gly Leu Leu Ser Ser Pro Gly Ala Ala Pro Ala Ser Ala Ala
     20                  25                  30

GTG ACC TCG GCT TCC GTG GTG CCG GCC CCG GCC GCG CCG GTG GCG TCT    199
Val Thr Ser Ala Ser Val Val Pro Ala Pro Ala Ala Pro Val Ala Ser
 35                  40                  45                  50

TCC TCG GCG GCC GCG GGC GGC GGG CGT CCC GGC CTG GGC AGA GGT CGG    247
Ser Ser Ala Ala Ala Gly Gly Gly Arg Pro Gly Leu Gly Arg Gly Arg
                 55                  60                  65

AAC AGT AGC AAA GGA CTG CCT CAG CCT ACG ATT TCT TTT GAT GGA ATC    295
Asn Ser Ser Lys Gly Leu Pro Gln Pro Thr Ile Ser Phe Asp Gly Ile
                 70                  75                  80

TAT GCA AAC GTG AGG ATG GTT CAT ATA CTT ACG TCA GTT GTT GGA TCG    343
Tyr Ala Asn Val Arg Met Val His Ile Leu Thr Ser Val Val Gly Ser
             85                  90                  95

AAA TGT GAA GTA CAA GTG AAA AAC GGA GGC ATA TAT GAA GGA GTT TTT    391
Lys Cys Glu Val Gln Val Lys Asn Gly Gly Ile Tyr Glu Gly Val Phe
            100                 105                 110

AAA ACA TAC AGT CCT AAG TGT GAC TTG GTA CTT GAT GCT GCA CAT GAG    439
Lys Thr Tyr Ser Pro Lys Cys Asp Leu Val Leu Asp Ala Ala His Glu
115                 120                 125                 130

AAA AGT ACA GAA TCC AGT TCG GGG CCA AAA CGT GAA GAA ATA ATG GAG    487
Lys Ser Thr Glu Ser Ser Ser Gly Pro Lys Arg Glu Glu Ile Met Glu
                135                 140                 145

AGT GTT TTG TTC AAA TGC TCA GAC TTC GTT GTG GTA CAG TTT AAA GAT    535
Ser Val Leu Phe Lys Cys Ser Asp Phe Val Val Val Gln Phe Lys Asp
            150                 155                 160

ACA GAC TCC AGT TAT GCA CGG AGA GAT GCT TTT ACT GAC TCT GCT CTC    583
Thr Asp Ser Ser Tyr Ala Arg Arg Asp Ala Phe Thr Asp Ser Ala Leu
                165                 170                 175

AGC GCA AAG GTG AAT GGT GAG CAC AAG GAG AAG GAC CTG GAG CCC TGG    631
Ser Ala Lys Val Asn Gly Glu His Lys Glu Lys Asp Leu Glu Pro Trp
180                 185                 190

GAT GCA GGG GAG CTC ACG GCC AGC GAG GAG CTG GAG CTG GAG AAT GAT    679
Asp Ala Gly Glu Leu Thr Ala Ser Glu Glu Leu Glu Leu Glu Asn Asp
195                 200                 205                 210

GTG TCT AAT GGA TGG GAC CCC AAT GAC ATG TTT CGA TAT AAT GAA GAG    727
Val Ser Asn Gly Trp Asp Pro Asn Asp Met Phe Arg Tyr Asn Glu Glu
                215                 220                 225

AAT TAT GGT GTG GTG TCC ACA TAT GAT AGC AGT TTA TCT TCA TAT ACG    775
Asn Tyr Gly Val Val Ser Thr Tyr Asp Ser Ser Leu Ser Ser Tyr Thr
                230                 235                 240

GTT CCT TTA GAA AGG GAC AAC TCA GAA GAA TTT CTT AAA CGG GAG GCA    823
Val Pro Leu Glu Arg Asp Asn Ser Glu Glu Phe Leu Lys Arg Glu Ala
            245                 250                 255

AGG GCA AAC CAG TTA GCA GAA GAA ATT GAA TCC AGT GCT CAG TAC AAA    871
Arg Ala Asn Gln Leu Ala Glu Glu Ile Glu Ser Ser Ala Gln Tyr Lys
            260                 265                 270

GCT CGT GTC GCC CTT GAG AAT GAT GAC CGG AGT GAG GAA GAA AAA TAC    919
Ala Arg Val Ala Leu Glu Asn Asp Asp Arg Ser Glu Glu Glu Lys Tyr
275                 280                 285                 290

ACA GCA GTC CAG AGA AAC TGC AGT GAC CGG GAG GGG CAT GGC CCC AAC    967
Thr Ala Val Gln Arg Asn Cys Ser Asp Arg Glu Gly His Gly Pro Asn
                295                 300                 305

ACT AGG GAC AAT AAA TAT ATT CCT CCT GGA CAA AGA AAC AGA GAA GTC   1015
Thr Arg Asp Asn Lys Tyr Ile Pro Pro Gly Gln Arg Asn Arg Glu Val
                310                 315                 320

CTA TCC TGG GGA AGT GGG AGA CAG AGC TCA CCA CGG ATG GGC CAG CCT   1063
Leu Ser Trp Gly Ser Gly Arg Gln Ser Ser Pro Arg Met Gly Gln Pro
            325                 330                 335
```

-continued

```
GGG CCA GGC TCC ATG CCG TCA AGA GCT GCT TCT CAC ACT TCA GAT TTC    1111
Gly Pro Gly Ser Met Pro Ser Arg Ala Ala Ser His Thr Ser Asp Phe
340             345                 350

AAC CCG AAC GCT GGC TCA GAC CAA AGA GTA GTT AAT GGA GGT GTT CCC    1159
Asn Pro Asn Ala Gly Ser Asp Gln Arg Val Val Asn Gly Gly Val Pro
355             360                 365                 370

TGG CCA TCG CCT TGC CCA TCT CAT TCC TCT CGC CCA CCT TCT CGC TAC    1207
Trp Pro Ser Pro Cys Pro Ser His Ser Ser Arg Pro Pro Ser Arg Tyr
                375                 380                 385

CAG TCA GGT CCC AAC TCT CTT CCA CCT CGG GCA GCC ACC CAT ACA CGG    1255
Gln Ser Gly Pro Asn Ser Leu Pro Pro Arg Ala Ala Thr His Thr Arg
            390                 395                 400

CCG CCC TCC AGG CCC CCC TCG AGG CCA TCC AGA CCC CCG TCT CAC CCC    1303
Pro Pro Ser Arg Pro Pro Ser Arg Pro Ser Arg Pro Pro Ser His Pro
        405                 410                 415

TCT GCT CAT GGT TCT CCA GCT CCT GTC TCT ACT ATG CCT AAA CGC ATG    1351
Ser Ala His Gly Ser Pro Ala Pro Val Ser Thr Met Pro Lys Arg Met
420                 425                 430

TCT TCA GAA GGA CCC CCA AGG ATG TCT CCA AAG GCA CAG CGC CAC CCT    1399
Ser Ser Glu Gly Pro Pro Arg Met Ser Pro Lys Ala Gln Arg His Pro
435             440                 445                 450

CGG AAT CAC AGA GTC TCT GCT GGG AGA GGC TCC ATG TCT AGT GGC CTA    1447
Arg Asn His Arg Val Ser Ala Gly Arg Gly Ser Met Ser Ser Gly Leu
                455                 460                 465

GAA TTT GTA TCC CAC AAT CCC CCA AGT GAA GCA GCT GCT CCT CCA GTG    1495
Glu Phe Val Ser His Asn Pro Pro Ser Glu Ala Ala Ala Pro Pro Val
                470                 475                 480

GCA AGG ACC AGT CCT GCA GGG GGA ACG TGG TCC TCA GTG GTC AGT GGG    1543
Ala Arg Thr Ser Pro Ala Gly Gly Thr Trp Ser Ser Val Val Ser Gly
            485                 490                 495

GTT CCA AGG TTA TCT CCC AAA ACT CAC AGA CCC AGG TCT CCC AGG CAG    1591
Val Pro Arg Leu Ser Pro Lys Thr His Arg Pro Arg Ser Pro Arg Gln
500                 505                 510

AGC AGC ATT GGA AAC TCT CCC AGC GGG CCT GTG CTT GCT TCT CCC CAA    1639
Ser Ser Ile Gly Asn Ser Pro Ser Gly Pro Val Leu Ala Ser Pro Gln
515             520                 525                 530

GCT GGC ATC ATC CCT GCA GAA GCC GTT TCC ATG CCT GTT CCC GCC GCA    1687
Ala Gly Ile Ile Pro Ala Glu Ala Val Ser Met Pro Val Pro Ala Ala
                535                 540                 545

TCT CCG ACT CCT GCC AGC CCT GCA TCC AAC AGA GCA CTG ACC CCA TCT    1735
Ser Pro Thr Pro Ala Ser Pro Ala Ser Asn Arg Ala Leu Thr Pro Ser
            550                 555                 560

ATT GAG GCA AAA GAT TCC AGG CTT CAA GAT CAG AGG CAG AAC TCT CCT    1783
Ile Glu Ala Lys Asp Ser Arg Leu Gln Asp Gln Arg Gln Asn Ser Pro
        565                 570                 575

GCA GGG AGT AAA GAA AAT GTT AAA GCA AGT GAA ACA TCA CCT AGC TTT    1831
Ala Gly Ser Lys Glu Asn Val Lys Ala Ser Glu Thr Ser Pro Ser Phe
    580                 585                 590

TCA AAA GCT GAC AAC AAA GGT ATG TCA CCA GTT GTT TCT GAA CAC AGA    1879
Ser Lys Ala Asp Asn Lys Gly Met Ser Pro Val Val Ser Glu His Arg
595                 600                 605                 610

AAA CAG ATT GAT GAC TTA AAG AAG TTT AAG AAT GAT TTT AGG TTA CAG    1927
Lys Gln Ile Asp Asp Leu Lys Lys Phe Lys Asn Asp Phe Arg Leu Gln
                615                 620                 625

CCA AGC TCT ACA TCT GAA TCT ATG GAT CAA CTA CTA AGC AAA AAT AGA    1975
Pro Ser Ser Thr Ser Glu Ser Met Asp Gln Leu Leu Ser Lys Asn Arg
                630                 635                 640

GAA GGA GAA AAG TCA CGA GAT TTG ATT AAA GAT AAA ACG GAA GCA AGT    2023
Glu Gly Glu Lys Ser Arg Asp Leu Ile Lys Asp Lys Thr Glu Ala Ser
            645                 650                 655
```

-continued

```
GCT AAG GAT AGT TTC ATT GAC AGC AGC AGC AGC AGC AAC TGT ACC      2071
Ala Lys Asp Ser Phe Ile Asp Ser Ser Ser Ser Ser Asn Cys Thr
        660             665             670

AGT GGC AGC AGC AAG ACC AAC AGC CCT AGC ATC TCC CCT TCC ATG CTT  2119
Ser Gly Ser Ser Lys Thr Asn Ser Pro Ser Ile Ser Pro Ser Met Leu
675             680             685             690

AGT AAT GCA GAG CAC AAG AGG GGG CCT GAG GTC ACA TCC CAA GGG GTG  2167
Ser Asn Ala Glu His Lys Arg Gly Pro Glu Val Thr Ser Gln Gly Val
                695             700             705

CAG ACT TCC AGC CCA GCC TGC AAA CAA GAG AAG GAT GAC AGA GAA GAG  2215
Gln Thr Ser Ser Pro Ala Cys Lys Gln Glu Lys Asp Asp Arg Glu Glu
        710             715             720

AAG AAA GAC ACA ACA GAG CAG GTT AGG AAA TCG ACA TTG AAT CCC AAT  2263
Lys Lys Asp Thr Thr Glu Gln Val Arg Lys Ser Thr Leu Asn Pro Asn
725             730             735

GCA AAG GAG TTC AAC CCT CGT TCT TTC TCT CAG CCA AAG CCT TCT ACT  2311
Ala Lys Glu Phe Asn Pro Arg Ser Phe Ser Gln Pro Lys Pro Ser Thr
        740             745             750

ACC CCA ACG TCA CCT CGG CCT CAA GCA CAA CCC AGC CCA TCT ATG GTG  2359
Thr Pro Thr Ser Pro Arg Pro Gln Ala Gln Pro Ser Pro Ser Met Val
755             760             765             770

GGT CAT CAG CAG CCA GCT CCA GTG TAC ACT CAG CCT GTG TGC TTC GCA  2407
Gly His Gln Gln Pro Ala Pro Val Tyr Thr Gln Pro Val Cys Phe Ala
                775             780             785

CCC AAT ATG ATG TAT CCC GTC CCA GTG AGC CCG GGC GTA CAA CCT TTA  2455
Pro Asn Met Met Tyr Pro Val Pro Val Ser Pro Gly Val Gln Pro Leu
        790             795             800

TAC CCA ATA CCT ATG ACG CCC ATG CCT GTG AAC CAA GCC AAG ACA TAT  2503
Tyr Pro Ile Pro Met Thr Pro Met Pro Val Asn Gln Ala Lys Thr Tyr
805             810             815

AGA GCA GGT AAA GTA CCA AAT ATG CCC CAA CAG CGA CAA GAC CAA CAT  2551
Arg Ala Gly Lys Val Pro Asn Met Pro Gln Gln Arg Gln Asp Gln His
        820             825             830

CAT CAA AGC ACC ATG ATG CAC CCA GCC TCC GCG GCA GGG CCA CCC ATC  2599
His Gln Ser Thr Met Met His Pro Ala Ser Ala Ala Gly Pro Pro Ile
835             840             845             850

GTA GCC ACC CCG CCC GCT TAC TCC ACT CAG TAC GTT GCC TAC AGC CCT  2647
Val Ala Thr Pro Pro Ala Tyr Ser Thr Gln Tyr Val Ala Tyr Ser Pro
                855             860             865

CAG CAG TTT CCC AAT CAG CCT TTG GTC CAG CAT GTG CCG CAT TAT CAG  2695
Gln Gln Phe Pro Asn Gln Pro Leu Val Gln His Val Pro His Tyr Gln
        870             875             880

TCT CAG CAT CCT CAT GTG TAC AGT CCT GTC ATA CAA GGT AAT GCC AGG  2743
Ser Gln His Pro His Val Tyr Ser Pro Val Ile Gln Gly Asn Ala Arg
885             890             895

ATG ATG GCA CCA CCA GCA CAT GCT CAG CCT GGT TTA GTG TCT TCT TCA  2791
Met Met Ala Pro Pro Ala His Ala Gln Pro Gly Leu Val Ser Ser Ser
900             905             910

GCT GCT CAG TTC GGG GCT CAC GAG CAG ACG CAC GCC ATG TAT GCA TGT  2839
Ala Ala Gln Phe Gly Ala His Glu Gln Thr His Ala Met Tyr Ala Cys
915             920             925             930

CCC AAA TTA CCA TAC AAC AAG GAG ACA AGC CCT TCT TTC TAC TTT GCC  2887
Pro Lys Leu Pro Tyr Asn Lys Glu Thr Ser Pro Ser Phe Tyr Phe Ala
                935             940             945

ATT TCC ACC GGC TCC CTC GCT CAG CAG TAT GCA CAT CCT AAT GCC GCC  2935
Ile Ser Thr Gly Ser Leu Ala Gln Gln Tyr Ala His Pro Asn Ala Ala
        950             955             960

CTG CAT CCA CAT ACT CCC CAT CCT CAG CCT TCG GCC ACT CCC ACC GGA  2983
Leu His Pro His Thr Pro His Pro Gln Pro Ser Ala Thr Pro Thr Gly
```

```
        965             970            975
CAG CAG CAA AGC CAG CAT GGT GGA AGT CAC CCT GCA CCC AGT CCT GTT      3031
Gln Gln Gln Ser Gln His Gly Gly Ser His Pro Ala Pro Ser Pro Val
        980             985                990

CAG CAC CAT CAG CAC CAG GCT GCC CAG GCT CTT CAT CTG GCC AGT CCA      3079
Gln His His Gln His Gln Ala Ala Gln Ala Leu His Leu Ala Ser Pro
995             1000            1005                1010

CAG CAG CAG TCG GCC ATT TAT CAT GCG GGG CTG GCA CCA ACA CCA CCT      3127
Gln Gln Gln Ser Ala Ile Tyr His Ala Gly Leu Ala Pro Thr Pro Pro
                1015            1020                1025

TCC ATG ACA CCT GCC TCT AAT ACA CAG TCT CCA CAG AGC AGT TTC CCA      3175
Ser Met Thr Pro Ala Ser Asn Thr Gln Ser Pro Gln Ser Ser Phe Pro
            1030                1035            1040

GCA GCA CAA CAG ACA GTC TTC ACC ATC CAC CCT TCT CAT GTT CAG CCG      3223
Ala Ala Gln Gln Thr Val Phe Thr Ile His Pro Ser His Val Gln Pro
            1045                1050            1055

GCA TAC ACC ACC CCA CCC CAC ATG GCC CAC GTA CCT CAG GCT CAT GTA      3271
Ala Tyr Thr Thr Pro Pro His Met Ala His Val Pro Gln Ala His Val
            1060                1065            1070

CAG TCA GGA ATG GTT CCT TCT CAT CCA ACT GCC CAT GCG CCA ATG ATG      3319
Gln Ser Gly Met Val Pro Ser His Pro Thr Ala His Ala Pro Met Met
1075            1080                1085            1090

CTA ATG ACG ACA CAG CCA CCC GGT CCC AAG GCC GCC CTC GCT CAA AGT      3367
Leu Met Thr Thr Gln Pro Pro Gly Pro Lys Ala Ala Leu Ala Gln Ser
                1095            1100                1105

GCA CTA CAG CCC ATT CCA GTT TCG ACA ACA GCG CAT TTC CCT TAT ATG      3415
Ala Leu Gln Pro Ile Pro Val Ser Thr Thr Ala His Phe Pro Tyr Met
            1110            1115                1120

ACG CAC CCT TCA GTA CAA GCC CAC CAC CAA CAG CAG TTG TAA              3457
Thr His Pro Ser Val Gln Ala His His Gln Gln Gln Leu
                1125            1130            1135

GGCTGCCTTG GAGGAACCGA AAGGCCAAAT CCCTTCTTCC CTTCTCTGCT TCTGCCACCA    3517

GGAAGCACAG AAAACTAGAA CTTCATTGAT TTTGTTTTTT AAAAGATACA CTGATTTAAC    3577

ATCTGATAGG AATGCTAACA GCTCACTTGC AGTGGAGGAT GTTTTGGACC GAGTAGAGGC    3637

ATGTAGGGAC TTGTGGCTGT TCCATAATTC CATGTGCTGT TGCAGGGTCC TGCAAGTACC    3697

CAGCTCTGCT TGCTGAAACT GGAAGTTATT TATTTTTTAA TGGCCCTTGA GAGTCATGAA    3757

CACATCAGCT AGCAACAGAA GTAACAAGAG TGATTCTTGC T                       3798
```

(2) INFORMATION FOR SEQ ID NO: 5:

(i) SEQUENCE CHARACTERISTICS:
        (A) LENGTH: 1135 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ser Leu Lys Pro Gln Pro Gln Pro Pro Ala Pro Ala Thr Gly Arg
1               5               10                  15

Lys Pro Gly Gly Gly Leu Leu Ser Ser Pro Gly Ala Ala Pro Ala Ser
                20              25                  30

Ala Ala Val Thr Ser Ala Ser Val Pro Ala Pro Ala Ala Pro Val
            35              40                  45

Ala Ser Ser Ser Ala Ala Ala Gly Gly Gly Arg Pro Gly Leu Gly Arg
        50                  55              60

Gly Arg Asn Ser Ser Lys Gly Leu Pro Gln Pro Thr Ile Ser Phe Asp
```

-continued

```
              65                  70                  75                  80
Gly Ile Tyr Ala Asn Val Arg Met Val His Ile Leu Thr Ser Val Val
                        85                  90                  95
Gly Ser Lys Cys Glu Val Gln Val Lys Asn Gly Gly Ile Tyr Glu Gly
                    100                 105                 110
Val Phe Lys Thr Tyr Ser Pro Lys Cys Asp Leu Val Leu Asp Ala Ala
                115                 120                 125
His Glu Lys Ser Thr Glu Ser Ser Gly Pro Lys Arg Glu Ile
            130                 135                 140
Met Glu Ser Val Leu Phe Lys Cys Ser Asp Phe Val Val Gln Phe
145                 150                 155                 160
Lys Asp Thr Asp Ser Ser Tyr Ala Arg Arg Asp Ala Phe Thr Asp Ser
                165                 170                 175
Ala Leu Ser Ala Lys Val Asn Gly Glu His Lys Glu Lys Asp Leu Glu
                180                 185                 190
Pro Trp Asp Ala Gly Glu Leu Thr Ala Ser Glu Glu Leu Glu Leu Glu
                195                 200                 205
Asn Asp Val Ser Asn Gly Trp Asp Pro Asn Asp Met Phe Arg Tyr Asn
210                 215                 220
Glu Glu Asn Tyr Gly Val Val Ser Thr Tyr Asp Ser Ser Leu Ser Ser
225                 230                 235                 240
Tyr Thr Val Pro Leu Glu Arg Asp Asn Ser Glu Glu Phe Leu Lys Arg
                245                 250                 255
Glu Ala Arg Ala Asn Gln Leu Ala Glu Glu Ile Glu Ser Ser Ala Gln
                260                 265                 270
Tyr Lys Ala Arg Val Ala Leu Glu Asn Asp Asp Arg Ser Glu Glu Glu
                275                 280                 285
Lys Tyr Thr Ala Val Gln Arg Asn Cys Ser Asp Arg Glu Gly His Gly
                290                 295                 300
Pro Asn Thr Arg Asp Asn Lys Tyr Ile Pro Pro Gly Gln Arg Asn Arg
305                 310                 315                 320
Glu Val Leu Ser Trp Gly Ser Gly Arg Gln Ser Ser Pro Arg Met Gly
                325                 330                 335
Gln Pro Gly Pro Gly Ser Met Pro Ser Arg Ala Ala Ser His Thr Ser
                340                 345                 350
Asp Phe Asn Pro Asn Ala Gly Ser Asp Gln Arg Val Asn Gly Gly
                355                 360                 365
Val Pro Trp Pro Ser Pro Cys Pro Ser His Ser Arg Pro Pro Ser
            370                 375                 380
Arg Tyr Gln Ser Gly Pro Asn Ser Leu Pro Pro Arg Ala Ala Thr His
385                 390                 395                 400
Thr Arg Pro Pro Ser Arg Pro Pro Ser Arg Pro Ser Arg Pro Pro Ser
                405                 410                 415
His Pro Ser Ala His Gly Ser Pro Ala Pro Val Ser Thr Met Pro Lys
                420                 425                 430
Arg Met Ser Ser Glu Gly Pro Pro Arg Met Ser Pro Lys Ala Gln Arg
                435                 440                 445
His Pro Arg Asn His Arg Val Ser Ala Gly Arg Gly Ser Met Ser Ser
                450                 455                 460
Gly Leu Glu Phe Val Ser His Asn Pro Pro Ser Glu Ala Ala Pro
465                 470                 475                 480
Pro Val Ala Arg Thr Ser Pro Ala Gly Gly Thr Trp Ser Ser Val Val
                485                 490                 495
```

```
Ser Gly Val Pro Arg Leu Ser Pro Lys Thr His Arg Pro Arg Ser Pro
        500                 505                 510

Arg Gln Ser Ser Ile Gly Asn Ser Pro Ser Gly Pro Val Leu Ala Ser
        515                 520                 525

Pro Gln Ala Gly Ile Ile Pro Ala Glu Ala Val Ser Met Pro Val Pro
        530                 535                 540

Ala Ala Ser Pro Thr Pro Ala Ser Pro Ala Ser Asn Arg Ala Leu Thr
545                 550                 555                 560

Pro Ser Ile Glu Ala Lys Asp Ser Arg Leu Gln Asp Gln Arg Gln Asn
                565                 570                 575

Ser Pro Ala Gly Ser Lys Glu Asn Val Lys Ala Ser Glu Thr Ser Pro
        580                 585                 590

Ser Phe Ser Lys Ala Asp Asn Lys Gly Met Ser Pro Val Val Ser Glu
        595                 600                 605

His Arg Lys Gln Ile Asp Asp Leu Lys Lys Phe Lys Asn Asp Phe Arg
        610                 615                 620

Leu Gln Pro Ser Ser Thr Ser Glu Ser Met Asp Gln Leu Leu Ser Lys
625                 630                 635                 640

Asn Arg Glu Gly Glu Lys Ser Arg Asp Leu Ile Lys Asp Lys Thr Glu
                645                 650                 655

Ala Ser Ala Lys Asp Ser Phe Ile Asp Ser Ser Ser Ser Ser Ser Asn
                660                 665                 670

Cys Thr Ser Gly Ser Ser Lys Thr Asn Ser Pro Ser Ile Ser Pro Ser
        675                 680                 685

Met Leu Ser Asn Ala Glu His Lys Arg Gly Pro Glu Val Thr Ser Gln
        690                 695                 700

Gly Val Gln Thr Ser Ser Pro Ala Cys Lys Gln Glu Lys Asp Asp Arg
705                 710                 715                 720

Glu Glu Lys Lys Asp Thr Thr Glu Gln Val Arg Lys Ser Thr Leu Asn
                725                 730                 735

Pro Asn Ala Lys Glu Phe Asn Pro Arg Ser Phe Ser Gln Pro Lys Pro
                740                 745                 750

Ser Thr Thr Pro Thr Ser Pro Arg Pro Gln Ala Gln Pro Ser Pro Ser
        755                 760                 765

Met Val Gly His Gln Gln Pro Ala Pro Val Tyr Thr Gln Pro Val Cys
        770                 775                 780

Phe Ala Pro Asn Met Met Tyr Pro Val Pro Val Ser Pro Gly Val Gln
785                 790                 795                 800

Pro Leu Tyr Pro Ile Pro Met Thr Pro Met Pro Val Asn Gln Ala Lys
                805                 810                 815

Thr Tyr Arg Ala Gly Lys Val Pro Asn Met Pro Gln Gln Arg Gln Asp
                820                 825                 830

Gln His His Gln Ser Thr Met Met His Pro Ala Ser Ala Ala Gly Pro
        835                 840                 845

Pro Ile Val Ala Thr Pro Ala Tyr Ser Thr Gln Tyr Val Ala Tyr
        850                 855                 860

Ser Pro Gln Gln Phe Pro Asn Gln Pro Leu Val Gln His Val Pro His
865                 870                 875                 880

Tyr Gln Ser Gln His Pro His Val Tyr Ser Pro Val Ile Gln Gly Asn
                885                 890                 895

Ala Arg Met Met Ala Pro Pro Ala His Ala Gln Pro Gly Leu Val Ser
                900                 905                 910
```

```
Ser Ser Ala Ala Gln Phe Gly Ala His Glu Gln Thr His Ala Met Tyr
        915                 920                 925
Ala Cys Pro Lys Leu Pro Tyr Asn Lys Glu Thr Ser Pro Ser Phe Tyr
        930                 935                 940
Phe Ala Ile Ser Thr Gly Ser Leu Ala Gln Gln Tyr Ala His Pro Asn
945                 950                 955                 960
Ala Ala Leu His Pro His Thr Pro His Pro Gln Pro Ser Ala Thr Pro
            965                 970                 975
Thr Gly Gln Gln Gln Ser Gln His Gly Gly Ser His Pro Ala Pro Ser
            980                 985                 990
Pro Val Gln His His Gln His Gln Ala Ala Gln Ala Leu His Leu Ala
            995                1000                1005
Ser Pro Gln Gln Gln Ser Ala Ile Tyr His Ala Gly Leu Ala Pro Thr
           1010                1015                1020
Pro Pro Ser Met Thr Pro Ala Ser Asn Thr Gln Ser Pro Gln Ser Ser
1025                1030                1035                1040
Phe Pro Ala Ala Gln Gln Thr Val Phe Thr Ile His Pro Ser His Val
                1045                1050                1055
Gln Pro Ala Tyr Thr Thr Pro Pro His Met Ala His Val Pro Gln Ala
            1060                1065                1070
His Val Gln Ser Gly Met Val Pro Ser His Pro Thr Ala His Ala Pro
            1075                1080                1085
Met Met Leu Met Thr Thr Gln Pro Pro Gly Pro Lys Ala Ala Leu Ala
            1090                1095                1100
Gln Ser Ala Leu Gln Pro Ile Pro Val Ser Thr Thr Ala His Phe Pro
1105                1110                1115                1120
Tyr Met Thr His Pro Ser Val Gln Ala His His Gln Gln Gln Leu
            1125                1130                1135

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

GGGCCCCTCA CCATGTCG                                                   18

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

CGGGCTTGCG GACATTGG                                                   18

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
```

(D) TOPOLOGY: linear (ii) MOLECULE TYPE: other nucleic acid (xi) SEQUENCE DESCRIPTION: SEQ ID NO: 8:

CCGCGGCTGC CAATGTCC                                                         18

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

GTAACCGTTC GGCGCCCG                                                         18

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

GGCTCCCGGC GGCTCCTT                                                         18

(2) INFORMATION FOR SEQ ID NO: 11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

TGCTGCTGCT GCTGGGGCTT CAG                                                   23

(2) INFORMATION FOR SEQ ID NO: 12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

CCGCCCGCTC CTCACGTGT                                                        19

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

ACCCCCGAGA AAGCAACC                                                     18

(2) INFORMATION FOR SEQ ID NO: 14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

CCGTTGCCGT TGCTACCA                                                     18

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

TTCTCATGTG CGGCATCAAG                                                   20

(2) INFORMATION FOR SEQ ID NO: 16:

(i) SEQUENCE CHARACTERISTICS:
        (A) LENGTH: 346 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Val Tyr Gly Pro Leu Thr Met Ser Leu Lys Pro Gln Gln Gln Gln Gln
1               5                   10                  15

Gln Gln Gln Gln Gln Gln Gln Gln Gln Gln Gln Gln Gln Gln Gln Gln
            20                  25                  30

Gln Pro Pro Ala Ala Ala Asn Val Arg Lys Pro Gly Gly Ser Gly
        35                  40                  45

Leu Leu Ala Ser Pro Ala Ala Pro Ser Pro Ser Ser Ser Ser Val
50                  55                  60

Ser Ser Ser Ala Thr Ala Pro Ser Ser Val Val Ala Ala Thr Ser
65                  70                  75                  80

Gly Gly Gly Arg Pro Gly Leu Gly Arg Gly Arg Asn Ser Asn Lys Gly
                85                  90                  95

Leu Pro Gln Ser Thr Ile Ser Phe Asp Gly Ile Tyr Ala Asn Met Arg
                100                 105                 110

Met Val His Ile Leu Thr Ser Val Val Gly Ser Lys Cys Glu Val Gln
                115                 120                 125

Val Lys Asn Gly Gly Ile Tyr Glu Gly Val Phe Lys Thr Tyr Ser Pro
                130                 135                 140

Lys Cys Asp Leu Val Leu Asp Ala Ala His Glu Lys Ser Thr Glu Ser
145                 150                 155                 160

Ser Ser Gly Pro Lys Arg Glu Glu Ile Met Glu Ser Ile Leu Phe Lys
                165                 170                 175

```
Cys Ser Asp Phe Val Val Gln Phe Lys Asp Met Asp Ser Ser Tyr
                180             185             190

Ala Lys Arg Asp Ala Phe Thr Asp Ser Ala Ile Ser Ala Lys Val Asn
        195             200             205

Gly Glu His Lys Glu Lys Asp Leu Glu Pro Trp Asp Ala Gly Glu Leu
            210             215             220

Thr Ala Asn Glu Glu Leu Glu Ala Leu Glu Asn Asp Val Ser Asn Gly
225             230             235             240

Trp Asp Pro Asn Asp Met Phe Arg Tyr Asn Glu Glu Asn Tyr Gly Val
                245             250             255

Val Ser Thr Tyr Asp Ser Ser Leu Ser Ser Tyr Thr Val Pro Leu Glu
            260             265             270

Arg Asp Asn Ser Glu Glu Phe Leu Lys Arg Glu Ala Arg Ala Asn Gln
                275             280             285

Leu Ala Glu Glu Ile Glu Ser Ser Ala Gln Tyr Lys Ala Arg Val Ala
            290             295             300

Leu Glu Asn Asp Asp Arg Ser Glu Glu Glu Lys Tyr Thr Ala Val Gln
305             310             315             320

Arg Asn Ser Ser Glu Arg Glu Gly His Ser Ile Asn Thr Arg Glu Asn
                325             330             335

Lys Tyr Ile Pro Pro Gly Gln Arg Asn Arg
            340             345

(2) INFORMATION FOR SEQ ID NO: 17:

(i) SEQUENCE CHARACTERISTICS:
        (A) LENGTH: 326 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

His Glu Gly Pro Leu Thr Met Ser Leu Lys Pro Gln Pro Gln Pro Pro
1               5                   10                  15

Ala Pro Ala Thr Gly Arg Lys Pro Gly Gly Leu Leu Ser Ser Pro
            20                  25                  30

Gly Ala Ala Pro Ala Ser Ala Ala Val Thr Ser Ala Ser Val Val Pro
            35                  40                  45

Ala Pro Ala Ala Pro Val Ala Ser Ser Ala Ala Ala Gly Gly Gly
        50                  55                  60

Arg Pro Gly Leu Gly Arg Gly Arg Asn Ser Ser Lys Gly Leu Pro Gln
65              70                  75                  80

Pro Thr Ile Ser Phe Asp Gly Ile Tyr Ala Asn Val Arg Met Val His
                85                  90                  95

Ile Leu Thr Ser Val Val Gly Ser Lys Cys Glu Val Gln Val Lys Asn
            100                 105                 110

Gly Gly Ile Tyr Glu Gly Val Phe Lys Thr Tyr Ser Pro Lys Cys Asp
            115                 120                 125

Leu Val Leu Asp Ala Ala His Glu Lys Ser Thr Glu Ser Ser Ser Gly
        130                 135                 140

Pro Lys Arg Glu Glu Ile Met Glu Ser Val Leu Phe Lys Cys Ser Asp
145                 150                 155                 160

Phe Val Val Val Gln Phe Lys Asp Thr Asp Ser Ser Tyr Ala Arg Arg
                165                 170                 175
```

```
Asp Ala Phe Thr Asp Ser Ala Leu Ser Ala Lys Val Asn Gly Glu His
            180                 185                 190

Lys Glu Lys Asp Leu Glu Pro Trp Asp Ala Gly Glu Leu Thr Ala Ser
            195                 200                 205

Glu Glu Leu Glu Leu Glu Asn Asp Val Ser Asn Gly Trp Asp Pro Asn
            210                 215                 220

Asp Met Phe Arg Tyr Asn Glu Glu Asn Tyr Gly Val Val Ser Thr Tyr
225                 230                 235                 240

Asp Ser Ser Leu Ser Ser Tyr Thr Val Pro Leu Glu Arg Asp Asn Ser
                245                 250                 255

Glu Glu Phe Leu Lys Arg Glu Ala Arg Ala Asn Gln Leu Ala Glu Glu
            260                 265                 270

Ile Glu Ser Ser Ala Gln Tyr Lys Ala Arg Val Ala Leu Glu Asn Asp
            275                 280                 285

Asp Arg Ser Glu Glu Lys Tyr Thr Ala Val Gln Arg Asn Cys Ser
290                 295                 300

Asp Arg Glu Gly His Gly Pro Asn Thr Arg Asp Asn Lys Tyr Ile Pro
305                 310                 315                 320

Pro Gly Gln Arg Asn Arg
                325

(2) INFORMATION FOR SEQ ID NO: 18:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

Leu Ala Pro Gln Pro Pro Pro Gln Gln His Gln Glu Arg Pro Gly
1               5                   10                  15

Ala Ala Ala Ile Gly Ser Ala Arg Gly Gln Ser Thr Gly Lys Gly Pro
            20                  25                  30

Pro Gln Ser Pro Val Phe Glu Gly Val Tyr Asn Asn Ser Arg Met Leu
            35                  40                  45

His Phe Leu Thr Ala Val Val Gly Ser Thr Cys Asp Val Lys Val Lys
        50                  55                  60

Asn Gly Thr Thr Tyr Glu Gly Ile Phe Lys Thr Leu Ser Ser Lys Phe
65                  70                  75                  80

Glu Leu Ala Val Asp Ala Val His Arg Lys Ala Ser Glu Pro Ala Gly
                85                  90                  95

Gly Pro Arg Arg Glu Asp Ile Val Asp Thr Met Val Phe Lys Pro Ser
            100                 105                 110

Asp Val Met Leu Val His Phe Arg Asn Val Asp Phe Asn Tyr Ala Thr
            115                 120                 125

Lys Asp Lys Phe Thr Asp Ser Ala Ile Ala Met Asn Ser Lys Val Asn
        130                 135                 140

Gly Glu His Lys Glu Lys Val Leu Gln Arg Trp Glu Gly Gly Asp Ser
145                 150                 155                 160

Asn Ser Asp Asp Tyr Asp Leu Glu Ser Asp Met Ser Asn Gly Trp Asp
                165                 170                 175

Pro Asn Glu Met Phe Lys Phe Asn Glu Glu Asn Tyr Gly Val Lys Thr
            180                 185                 190
```

```
Thr Tyr Asp Ser Ser Leu Ser Ser Tyr Thr Val Pro Leu Glu Lys Asp
        195                 200                 205

Asn Ser Glu Glu Phe Arg Gln Arg Glu Leu Arg Ala Ala Gln Leu Ala
    210                 215                 220

Arg Glu Ile Glu Ser Ser Pro Gln Tyr Arg Leu Arg Ile Ala Met Glu
225                 230                 235                 240

Asn Asp Asp Gly Arg Thr Glu Glu Lys His Ser Ala Val Gln Arg
                245                 250                 255

Gln Gly Ser Gly Arg Glu Ser Pro Ser Leu Ala Ser Arg Glu Gly Lys
            260                 265                 270

Tyr Ile Pro
        275

(2) INFORMATION FOR SEQ ID NO: 19:

(i) SEQUENCE CHARACTERISTICS:
        (A) LENGTH: 1257 base pairs
        (B) TYPE: nucleic acid
        (C) STRANDEDNESS: both
        (D) TOPOLOGY: both (ii) MOLECULE TYPE: cDNA (ix) FEATURE:
         (A) NAME/KEY: CDS
         (B) LOCATION: 2..1255

(xi) SEQUENCE DESCRIPTION: SEQ ID NO: 19:

G CAC GAG GGG CCG CTC ACC ATG TCG CTG AAG CCG CAG CCG CAG CCG           46
  His Glu Gly Pro Leu Thr Met Ser Leu Lys Pro Gln Pro Gln Pro
   1               5                  10                  15

CCC GCG CCC GCC ACT GGC CGC AAG CCC GGC GGC GGC CTG CTC TCG TCG         94
Pro Ala Pro Ala Thr Gly Arg Lys Pro Gly Gly Gly Leu Leu Ser Ser
                20                  25                  30

CCC GGC GCC GCG CCG GCC TCG GCC GCG GTG ACC TCG GCT TCC GTG GTG        142
Pro Gly Ala Ala Pro Ala Ser Ala Ala Val Thr Ser Ala Ser Val Val
            35                  40                  45

CCG GCC CCG GCC GCG CCG GTG GCG TCT TCC TCG GCG GCC GCG GGC GGC        190
Pro Ala Pro Ala Ala Pro Val Ala Ser Ser Ser Ala Ala Ala Gly Gly
        50                  55                  60

GGG CGT CCC GGC CTG GGC AGA GGT CGG AAC AGT AGC AAA GGA CTG CCT        238
Gly Arg Pro Gly Leu Gly Arg Gly Arg Asn Ser Ser Lys Gly Leu Pro
    65                  70                  75

CAG CCT ACG ATT TCT TTT GAT GGA ATC TAT GCA AAC GTG AGG ATG GTT        286
Gln Pro Thr Ile Ser Phe Asp Gly Ile Tyr Ala Asn Val Arg Met Val
 80                  85                  90                  95

CAT ATA CTT ACG TCA GTT GTT GGA TCG AAA TGT GAA GTA CAA GTG AAA        334
His Ile Leu Thr Ser Val Val Gly Ser Lys Cys Glu Val Gln Val Lys
                100                 105                 110

AAC GGA GGC ATA TAT GAA GGA GTT TTT AAA ACA TAC AGT CCT AAG TGT        382
Asn Gly Gly Ile Tyr Glu Gly Val Phe Lys Thr Tyr Ser Pro Lys Cys
            115                 120                 125

GAC TTG GTA CTT GAT GCT GCA CAT GAG AAA AGT ACA GAA TCC AGT TCG        430
Asp Leu Val Leu Asp Ala Ala His Glu Lys Ser Thr Glu Ser Ser Ser
        130                 135                 140

GGG CCA AAA CGT GAA GAA ATA ATG GAG AGT GTT TTG TTC AAA TGC TCA        478
Gly Pro Lys Arg Glu Glu Ile Met Glu Ser Val Leu Phe Lys Cys Ser
    145                 150                 155

GAC TTC GTT GTG GTA CAG TTT AAA GAT ACA GAC TCC AGT TAT GCA CGG        526
Asp Phe Val Val Val Gln Phe Lys Asp Thr Asp Ser Ser Tyr Ala Arg
160                 165                 170                 175
```

-continued

| | | |
|---|---|---|
| AGA GAT GCT TTT ACT GAC TCT GCT CTC AGC GCA AAG GTG AAT GGT GAG<br>Arg Asp Ala Phe Thr Asp Ser Ala Leu Ser Ala Lys Val Asn Gly Glu<br>            180                         185                     190 | 574 |
| CAC AAG GAG AAG GAC CTG GAG CCC TGG GAT GCA GGG GAG CTC ACG GCC<br>His Lys Glu Lys Asp Leu Glu Pro Trp Asp Ala Gly Glu Leu Thr Ala<br>                195                     200                     205 | 622 |
| AGC GAG GAG CTG GAG CTG GAG AAT GAT GTG TCT AAT GGA TGG GAC CCC<br>Ser Glu Glu Leu Glu Leu Glu Asn Asp Val Ser Asn Gly Trp Asp Pro<br>         210                        215                     220 | 670 |
| AAT GAC ATG TTT CGA TAT AAT GAA GAG AAT TAT GGT GTG GTG TCC ACA<br>Asn Asp Met Phe Arg Tyr Asn Glu Glu Asn Tyr Gly Val Val Ser Thr<br>225                         230                     235 | 718 |
| TAT GAT AGC AGT TTA TCT TCA TAT ACG GTT CCT TTA GAA AGG GAC AAC<br>Tyr Asp Ser Ser Leu Ser Ser Tyr Thr Val Pro Leu Glu Arg Asp Asn<br>240                         245                     250                     255 | 766 |
| TCA GAA GAA TTT CTT AAA CGG GAG GCA AGG GCA AAC CAG TTA GCA GAA<br>Ser Glu Glu Phe Leu Lys Arg Glu Ala Arg Ala Asn Gln Leu Ala Glu<br>                260                     265                     270 | 814 |
| GAA ATT GAA TCC AGT GCT CAG TAC AAA GCT CGT GTC GCC CTT GAG AAT<br>Glu Ile Glu Ser Ser Ala Gln Tyr Lys Ala Arg Val Ala Leu Glu Asn<br>                  275                     280                     285 | 862 |
| GAT GAC CGG AGT GAG GAA GAA AAA TAC ACA GCA GTC CAG AGA AAC TGC<br>Asp Asp Arg Ser Glu Glu Glu Lys Tyr Thr Ala Val Gln Arg Asn Cys<br>         290                        295                     300 | 910 |
| AGT GAC CGG GAG GGG CAT GGC CCC AAC ACT AGG GAC AAT AAA TAT ATT<br>Ser Asp Arg Glu Gly His Gly Pro Asn Thr Arg Asp Asn Lys Tyr Ile<br>305                         310                     315 | 958 |
| CCT CCT GGA CAA AGA AAC AGA GAA GTC CTA TCC TGG GGA AGT GGG AGA<br>Pro Pro Gly Gln Arg Asn Arg Glu Val Leu Ser Trp Gly Ser Gly Arg<br>320                         325                     330                     335 | 1006 |
| CAG AGC TCA CCA CGG ATG GGC CAG CCT GGG CCA GGC TCC ATG CCG TCA<br>Gln Ser Ser Pro Arg Met Gly Gln Pro Gly Pro Gly Ser Met Pro Ser<br>                340                     345                     350 | 1054 |
| AGA GCT GCT TCT CAC ACT TCA GAT TTC AAC CCG AAC GCT GGC TCA GAC<br>Arg Ala Ala Ser His Thr Ser Asp Phe Asn Pro Asn Ala Gly Ser Asp<br>                355                     360                     365 | 1102 |
| CAA AGA GTA GTT AAT GGA GGT GTT CCC TGG CCA TCG CCT TGC CCA TCT<br>Gln Arg Val Val Asn Gly Gly Val Pro Trp Pro Ser Pro Cys Pro Ser<br>         370                        375                     380 | 1150 |
| CCT TCC TCT CGC CCA CCT TCT CGC TAC CAG TCA GGT CCC AAC TCT CTT<br>Pro Ser Ser Arg Pro Pro Ser Arg Tyr Gln Ser Gly Pro Asn Ser Leu<br>385                         390                     395 | 1198 |
| CCA CCT CGG GCA GCC ACC CCT ACA CGG CCT CGT GCC GAA TTC CTG CAG<br>Pro Pro Arg Ala Ala Thr Pro Thr Arg Pro Arg Ala Glu Phe Leu Gln<br>400                         405                     410                     415 | 1246 |
| CCC GGG GAT CC<br>Pro Gly Asp | 1257 |

That which is claimed is:

1. An isolated nucleic acid encoding the amino acid sequence set forth at SEQ ID NO:5.

2. An isolated nucleic acid set forth at SEQ ID NO:4 encoding an SCA2 polypeptide.

3. An isolated nucleic acid comprising nucleotides 163–4098 of SEQ ID NO:2.

4. An isolated nucleic acid encoding the amino acid sequence set forth at SEQ ID NO:3.

5. An isolated nucleic acid comprising nucleotides 50–3454 of SEQ ID NO:4.

6. An isolated nucleic acid comprising the nucleic acid sequence set forth at SEQ ID NO:19.

7. A vector comprising DNA according to claim 4.

8. A vector comprising DNA according to claim 1.

* * * * *